(12) United States Patent
Joung et al.

(10) Patent No.: US 11,891,631 B2
(45) Date of Patent: Feb. 6, 2024

(54) TRANSCRIPTION ACTIVATOR-LIKE EFFECTOR (TALE) - LYSINE-SPECIFIC DEMETHYLASE 1 (LSD1) FUSION PROTEINS

(71) Applicant: The General Hospital Corporation, Boston, MA (US)

(72) Inventors: Jae Keith Joung, Winchester, MA (US); Eric M. Mendenhall, Madison, AL (US); Bradley E. Bernstein, Cambridge, MA (US); Deepak Reyon, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 1292 days.

(21) Appl. No.: 16/376,736

(22) Filed: Apr. 5, 2019

(65) Prior Publication Data
US 2019/0359951 A1 Nov. 28, 2019

Related U.S. Application Data

(63) Continuation of application No. 14/435,065, filed as application No. PCT/US2013/064511 on Oct. 11, 2013, now abandoned.

(60) Provisional application No. 61/865,432, filed on Aug. 13, 2013, provisional application No. 61/776,039, filed on Mar. 11, 2013, provisional application No. 61/713,098, filed on Oct. 12, 2012.

(51) Int. Cl.
| | | |
|---|---|---|
| *C12N 9/02* | (2006.01) | |
| *C07K 14/195* | (2006.01) | |
| *C12N 9/06* | (2006.01) | |
| *C12N 9/22* | (2006.01) | |
| *A61K 38/00* | (2006.01) | |
| *C12N 15/63* | (2006.01) | |
| *C12N 5/10* | (2006.01) | |
| *C12N 15/10* | (2006.01) | |

(52) U.S. Cl.
CPC .......... *C12N 9/0004* (2013.01); *C07K 14/195* (2013.01); *C12N 9/0026* (2013.01); *C12N 9/0083* (2013.01); *C12N 9/22* (2013.01); *C12Y 105/00* (2013.01); *C12Y 114/99* (2013.01); *A61K 38/00* (2013.01); *C07K 2319/80* (2013.01); *C12N 15/1093* (2013.01); *C12N 15/63* (2013.01)

(58) Field of Classification Search
CPC .......... C12Y 114/11001; C12Y 114/99; C12N 9/0083; C07K 2319/80
See application file for complete search history.

(56) References Cited

U.S. PATENT DOCUMENTS

| | | |
|---|---|---|
| 4,603,044 A | 7/1986 | Geho et al. |
| 4,797,368 A | 1/1989 | Carter et al. |
| 4,957,773 A | 9/1990 | Spencer et al. |
| 6,007,988 A | 12/1999 | Choo et al. |
| 6,013,453 A | 1/2000 | Choo et al. |
| 6,453,242 B1 | 9/2002 | Eisenberg et al. |
| 6,492,117 B1 | 12/2002 | Choo et al. |
| 6,503,717 B2 | 1/2003 | Case et al. |
| 6,511,808 B2 | 1/2003 | Wolffe et al. |
| 6,534,261 B1 | 3/2003 | Cox, III et al. |
| 7,001,768 B2 | 2/2006 | Wolfe et al. |
| 7,220,719 B2 | 5/2007 | Case |
| 7,741,086 B2 | 6/2010 | Shi |
| 7,914,796 B2 | 3/2011 | Miller |
| 8,034,598 B2 | 10/2011 | Miller |
| 8,071,370 B2 | 12/2011 | Wolffe |
| 8,771,986 B2 | 7/2014 | Miller |
| 8,962,281 B2 | 2/2015 | Doyon |
| 10,273,271 B2 | 4/2019 | Joung et al. |
| 10,676,749 B2 | 6/2020 | Joung et al. |
| 10,894,950 B2 | 1/2021 | Joung et al. |
| 2002/0160940 A1 | 1/2002 | Case et al. |
| 2002/0106680 A1 | 8/2002 | Shinmyo |
| 2002/0119498 A1 | 8/2002 | Joung et al. |
| 2002/0164575 A1 | 11/2002 | Case et al. |
| 2003/0083283 A1 | 5/2003 | Bennett et al. |
| 2006/0115850 A1 | 6/2006 | Schatz |
| 2008/0131962 A1 | 6/2008 | Miller |
| 2009/0133158 A1 | 5/2009 | Lahaye et al. |
| 2010/0132069 A1 | 5/2010 | Lahaye et al. |
| 2011/0059502 A1 | 3/2011 | Chalasani |
| 2011/0112040 A1 | 5/2011 | Liu et al. |
| 2011/0301073 A1 | 12/2011 | Gregory et al. |

(Continued)

FOREIGN PATENT DOCUMENTS

| | | |
|---|---|---|
| EP | 1941060 | 7/2008 |
| EP | 2206723 | 7/2010 |

(Continued)

OTHER PUBLICATIONS

Mendenhall, EM, Williamson, K, Reyon, D, Joung JK, and Bernstein BE. Identification of promoter targets of enhancers by epigenetic knockdown using TAL DNA binding proteins. Epigenetics & Chromatin, vol. 6, Suppl. 1, 012, Mar. 18, 2013, printed as pp. 1/2-2/2. (Year: 2013).*

(Continued)

*Primary Examiner* — Jennifer Dunston
(74) *Attorney, Agent, or Firm* — Fish & Richardson P.C.

(57) ABSTRACT

Fusion proteins comprising a DNA binding domain, e.g., a TAL effector repeat array (TALE) or zinc finger array, and a catalytic domain comprising a sequence that catalyzes histone demethylation, and methods of use thereof.

5 Claims, 13 Drawing Sheets

Specification includes a Sequence Listing.

(56) References Cited

U.S. PATENT DOCUMENTS

| | | |
|---|---|---|
| 2012/0064620 A1 | 3/2012 | Bonas |
| 2012/0100569 A1 | 4/2012 | Liu et al. |
| 2013/0323220 A1 | 12/2013 | Joung et al. |
| 2014/0274812 A1 | 9/2014 | Joung et al. |
| 2015/0376626 A1 | 12/2015 | Joung et al. |
| 2016/0010076 A1 | 1/2016 | Joung et al. |
| 2016/0024523 A1 | 1/2016 | Joung et al. |

FOREIGN PATENT DOCUMENTS

| | | |
|---|---|---|
| JP | 2003-501069 | 1/2003 |
| JP | 2003-531616 | 10/2003 |
| JP | 2013-529083 | 7/2013 |
| JP | 2015-527889 | 9/2015 |
| WO | WO 1991/016024 | 10/1991 |
| WO | WO 1991/017424 | 11/1991 |
| WO | WO 9319202 | 9/1993 |
| WO | WO 1993/024641 | 12/1993 |
| WO | WO 9517413 | 6/1995 |
| WO | WO 9810095 | 3/1998 |
| WO | WO 9947536 | 9/1999 |
| WO | WO 00/75368 | 12/2000 |
| WO | WO 2001/019981 | 3/2001 |
| WO | WO 2001/053480 | 7/2001 |
| WO | WO 0183732 | 11/2001 |
| WO | WO 2002/057308 | 7/2002 |
| WO | WO 2002/099084 | 12/2002 |
| WO | WO 2004/099366 | 11/2004 |
| WO | WO 2006/071608 | 7/2006 |
| WO | WO 2007/128982 | 11/2007 |
| WO | WO 2009/134409 | 11/2009 |
| WO | WO 2010/037001 | 4/2010 |
| WO | WO 2010/079430 | 7/2010 |
| WO | WO 2011/017293 | 2/2011 |
| WO | WO 2011/019385 | 2/2011 |
| WO | WO 2011/072246 | 6/2011 |
| WO | WO 2011/146121 | 11/2011 |
| WO | WO 2012/138939 | 10/2012 |
| WO | WO 2013/012674 | 1/2013 |
| WO | WO 2013/017950 | 2/2013 |

OTHER PUBLICATIONS

Wu et al. Identification and functional analysis of 9p24 amplified genes in human breast cancer. Oncogene. Vol. 31, pp. 333-341, 2012, published online Jun. 13, 2011. (Year: 2011).*
Akopian et al., "Chimeric recombinases with designed DNA sequence recognition," Proc Natl Acad Sci USA, Jul. 22, 2003;100(15):8688-91.
Alvarez and Curiel, "A phase I study of recombinant adenovirus vector-mediated intraperitoneal delivery of herpes simplex virus thymidine kinase (HSV-TK) gene and intravenous ganciclovir for previously treated ovarian and extraovarian cancer patients," Hum. Gene Ther., Mar. 1997, 5:597-613.
Anders and Huber, "Differential expression analysis for sequence count data," Genome Biol., 11(10):R106, Epub Oct. 27, 2010.
Arimondo et al., "Exploring the Cellular Activity of Camptothecin—Triple—Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
Aslanidis et al., "Ligation-independent cloning of PCR products (LIC-PCR)," Nucleic Acids Res., Oct. 25, 1990;18(20):6069-74.

Australian Office Action in Australian Application No. 2012284365, dated Jul. 29, 2016, 5 pages.
Bae et al., "Human zinc fingers as building blocks in the construction of artificial transcription factors," Nat Biotechnol., 21(3):275-280, Epub Feb. 18, 2003.
Bannister et al., "Histone methylation: Dynamic or static?," Cell, Jun. 28, 2002, 109(7): 801-806.
Batt, C.A., Chapter 14. Genetic Engineering of Food Proteins in Food Proteins and Their Applications, Damodaran, S., Ed. CRC Press, Mar. 12, 1997, p. 425.
Beerli and Barbas, "Engineering polydactyl zinc-finger transcription factors," Nat Biotechnol., 20(2):135-141, Feb. 2002.
Beerli et al., "Toward controlling gene expression at will: Specific regulation of the erbB-2/HER-2 promoter using polydactyl zinc finger proteins constructed from modular building blocks," PNAS, Dec. 1998, 95: 14628-14633.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bergmann et al. Epigenetic engineering shows H3K4me2 is required for HJURP targeting and CENP-A assembly on a synthetic human kinetochore. The EMBO Journal, vol. 30, pp. 328-340, Jan. 2011, published online Dec. 14, 2010, including pp. 1/14-14/14 of Supplementary Data.
Biancotto et al., "Histone modification therapy of cancer," Adv Genet., 70:341-386, 2010.
Bibikova et al., "Enhancing gene targeting with designed zinc finger nucleases," Science, May 2, 2003;300(5620):764.
Bibikova et al., "Stimulation of homologous recombination through targeted cleavage by chimeric nucleases," Mol Cell Biol., Jan. 2001;21(1):289-97.
Blaese et al., "T lymphocyte-directed gene therapy for ADA—SCID: initial trial results after 4 years," Science, Oct. 1995, 270(5235):475-480.
Blancafort et al., "Designing transcription factor architectures for drug discovery," Mol Pharmacol., 66(6):1361-1371, Epub Aug. 31, 2004.
Boch et al., "Breaking the code of DNA binding specificity of TAL-type III effectors," Science, 326(5959):1509-1512, Dec. 11, 2009.
Boch et al., "Xanthomonas AvrBs3 family-type III effectors: discovery and function," Annu Rev Phytopathol., 48:419-436, 2010.
Boch, "TALEs of genome targeting," Nat Biotechnol., 29(2):135-136, Feb. 2011.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Bonas et al., "Genetic and Structural Characterization of the Avirulence Gene AVR-BS3 From Xanthomonas-Campestris Pathovar Vesicatoria," Molecular and General Genetics, Jul. 1989, 218(1): 127-136.
Boyle et al., "High-resolution mapping and characterization of open chromatin across the genome," Cell., 132(2):311-322, Jan. 25, 2008.
Briggs et al., "Iterative capped assembly: rapid and scalable synthesis of repeat-module DNA such as TAL effectors from individual monomers," Nucleic Acids Res., Aug. 2012;40(15):e117.
Bulger and Groudine, "Functional and mechanistic diversity of distal transcription enhancers," Cell., 144(3):327-339, Feb. 4, 2011.
Bultmann et al., "Targeted transcriptional activation of silent oct4 pluripotency gene by combining designer TALEs and inhibition of epigenetic modifiers," Nucleic Acids Res., 40(12):5368-77. Epub Mar. 2, 2012.
Burnett et al., "Conditional macrophage ablation in transgenic mice expressing a Fas-based suicide gene," J. Leukoc. Biol., Apr. 2004, 75(4):612-623.
Cade et al., "Highly efficient generation of heritable zebrafish gene mutations using homo- and heterodimeric TALENs," Nucleic Acids Res., Sep. 2012, 40(16):8001-10.
Calo and Wysocka, "Modification of enhancer chromatin: what, how, and why?" Mol Cell., Mar. 2013, 49(5):825-837.

(56) References Cited

OTHER PUBLICATIONS

Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carey et al., "A mechanism for synergistic activation of a mammalian gene by GAL4 derivatives," Nature, 345(6273):361-364, May 24, 1990.
Caron et al., "Intracellular Delivery of a Tat-eGFP Fusion Protein into Muscle Cells," Mol Ther., Mar. 2001, 3:310-318.
Carroll et al., "Design, construction and in vitro testing of zinc finger nucleases," Nat Protoc., 1(3):1329-1341, 2006.
Carroll, "Progress and prospects: zinc-finger nucleases as gene therapy agents," Gene Ther., 15(22):1463-1468, Epub Sep. 11, 2008.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol Ther., 16(7):1200-1207, Epub Jun. 10, 2008.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PloS One, 7(9):E44852 pp. 1-11 (2012).
Chase et al., "Histone methylation at H3K9: evidence for a restrictive epigenome in schizophrenia," Schizophr Res., 149(1-3):15-20, Epub Jun. 28, 2013.
Chen et al., "Crystal structure of human histone lysine-specific demethylase 1 (LSD1)," Proc Natl Acad Sci U S A., 103(38):13956-13961, Epub Sep. 6, 2006.
Chen et al., "Fusion protein linkers: property, design and functionality," Adv Drug Deliv Rev., 65(10):1357-1369, [author manuscript] Epub Sep. 29, 2012.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Chim et al., "Methylation profiling in multiple myeloma," Leuk. Res., Apr. 2004, 28:379-85.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "The tracrRNA and Cas9 families of type II CRISPR-Cas immunity systems," RNA Biol., 10(5):726-737, Epub Apr. 5, 2013.
Coffman et al., "Improved renal function in mouse kidney allografts lacking MHC class I antigens," J. Immunol., Jul. 1993, 151:425-35.
Cong et al., "Comprehensive interrogation of natural TALE DNA-binding modules and transcriptional repressor domains," Nat Commun., 3:968, [author manuscript] Jul. 24, 2012.
Cong et al., "Multiplex genome engineering using CRISPR/Cas systems," Science, 339(6121):819-823, Epub Jan. 3, 2013.
Consortium, The ENCODE Project, "An integrated encyclopedia of DNA elements in the human genome," Nature, Sep. 2012, 488:57-74.
Copeland et al., "Targeting genetic alterations in protein methyltransferases for personalized cancer therapeutics," Oncogene., 32(8):939-946, Epub Nov. 19, 2012.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Creyghton et al., "Histone H3K27ac separates active from poised enhancers and predicts developmental state," Proc Natl Acad Sci U S A., 107(50):21931-21936, Epub Nov. 24, 2010.
Cronican et al., "A Class of Human Proteins that Deliver Functional Proteins into Mammalian Cells In Vitro and In Vivo," Chem Biol., Jul. 2011, 18:833-838.
Cronican et al., "Potent Delivery of Functional Proteins into Mammalian Cells in Vitro and in Vivo Using a Supercharged Protein," ACS Chem. Biol., 2010, 5:747.
d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
Davis, "Transcriptional regulation by MAP kinases," Mol Reprod Dev., Dec. 1995;42(4):459-67.
De Zhu, "The altered DNA methylation pattern and its implications in liver cancer," Cell. Res., 2005, 15:272-80.
Derossi et al., "The Third Helix of the Antennapedia Homeodomain Translocates through Biological Membranes," J. Biol. Chem., Apr. 1994, 269:10444.
Deshayes et al., "Cell-penetrating peptides: tools for intracellular delivery of therapeutics," Cell. Mol. Life Sci., Aug. 2005, 62:1839-49.
Dhami et al., "Genomic approaches uncover increasing complexities in the regulatory landscape at the human SCL (TAL1) locus," PLoS One, 5(2):e9059, Feb. 5, 2010.
Donnelly et al., "Targeted delivery of peptide epitopes to class I major histocompatibility molecules by a modified Pseudomonas exotoxin," PNAS, Apr. 1993, 90:3530-34.
Doyle et al., "TAL Effector-Nucleotide Targeter (TALE-NT) 2.0: tools for TAL effector design and target prediction," Nucleic Acids Res., 40(Web Server issue): W117-W122, Epub Jun. 12, 2012.
Doyle, Computational and experimental analysis of TAL effector-DNA binding [dissertation], Jan. 2013, Iowa State University, Ames, Iowa, 162 pages.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dreidax et al., "Low p14ARF expression in neuroblastoma cells is associated with repressed histone mark status, and enforced expression induces growth arrest and apoptosis," Hum Mol Genet., 22(9):1735-1745, May 1, 2013.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Eisenschmidt et al., "Developing a programmed restriction endonuclease for highly specific DNA cleavage," Nucleic Acids Res., 33(22):7039-47 (2005).
El-Andaloussi et al., "Cell-penetrating peptides: mechanisms and applications," Curr. Pharm. Des., 2005, 11:3597-3611.
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elliot and O'Hare, "Intercellular trafficking and protein delivery by a herpesvirus structural protein," Cell, 88(2):223-233, Jan. 24, 1997.
Elrod-Erickson et al., "High-resolution structures of variant Zif268-DNA complexes: implications for understanding zinc finger-DNA recognition," Structure, 6(4):451-464, Apr. 15, 1998.
Endoh et al., "Cellular siRNA delivery using TatU1A and photo-induced RNA interference," Methods Mol. Biol., 2010, 623:271-281.
Entry for CDKN2A, cyclin-dependent kinase inhibitor 2A [*Homo sapiens* (human)], Gene ID: 1029, updated on Oct. 31, 2016, and printed from http:www.ncbi.nlm.nih.gov/gene/1029 as p. 1/9 on Nov. 1, 2016.
Ernst, J. et al., "Mapping and analysis of chromatin state dynamics in nine human cell types," Nature, 2011, 473:43-49.
Esteller et al., "A Gene Hypermethylation Profile of Human Cancer," Cancer Res., Apr. 2001, 61:3225-9.

(56) References Cited

OTHER PUBLICATIONS

Esteller et al., "Promoter Hypermethylation and BRCA1 Inactivation in Sporadic Breast and Ovarian Tumors," J. Natl. Cancer Inst., Apr. 2000, 92:564-9.
European Office Action in Application No. 13797024.0, dated Mar. 16, 2018, 8 pages.
European Office Action in European Application No. 13797024.0, dated Jul. 18, 2017, 9 pages.
European Office Action in European Application No. 13845212, dated May 18, 2016, 1 page.
Evans et al., Binding, Regeneration of Plants, Plant Protoplasts, pp. 21-73 (1985).
Evans et al., Protoplasts Isolation and Culture, Handbook of Plant Cell Culture, pp. 124-176 (1983).
Extended European Search Report in Application No. 17205413.2, dated Mar. 23, 2018, 7 pages.
Extended European Search Report in Application No. 18191841.8, dated May 5, 2019, 9 pages.
Extended European Search Report in Application No. 18214166.3, dated Feb. 4, 2019, 9 pages.
Extended European Search Report in European Application No. 12814750.1, dated Jun. 30, 2015,13 pages.
Extended European Search Report in European Application No. 13797024, dated Mar. 15, 2016, 9 pages.
Extended European Search Report in European Application No. 13845212, dated Apr. 29, 2016, 6 pages.
Externded European Search Report in European Application No. 14749683, dated Sep. 9, 2016, 7 pages.
Fahraeus et al., "Inhibition of pRb phosphorylation and cell-cycle progression by a 20-residue peptide derived from p16CDKN2/INK4A," Curr Biol., 6(1):84-91, Jan. 1, 1996.
Foley et al., "Targeted mutagenesis in zebrafish using customized zinc-finger nucleases", Nature Protocols, Nature Publishing Group, Jan. 2009, 4(12):1855-1868.
Fonfara et al., "Creating highly specific nucleases by fusion of active restriction endonucleases and catalytically inactive homing endonucleases," Nucleic Acids Res., 40(2):847-860, Epub Sep. 29, 2011.
Frauer et al., "Different Binding Properties and Function of CXXC Zinc Finger Domains in Dnmt1 and Tet1," PLOS One, Feb. 2011, 6: e16627.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Futaki, "Oligoarginine vectors for intracellular delivery: design and cellular-uptake mechanisms," Biopolymers, 2006, 84:241-249.
Gao et al., "Hypermethylation of the RASSF1A gene in gliomas," Clin. Chim. Acta., Nov. 2004, 349:173-9.
Garcia-Bustos et al., "Nuclear protein localization," Biochim Biophys Acta., 1071(1):83-101, Mar. 7, 1991.
Garg et al., "Engineering synthetic TAL effectors with orthogonal target sites," Nucleic Acids Res., 40(15):7584-7595, Epub May 11, 2012.
Gavin et al., "Dimethylated lysine 9 of histone 3 is elevated in schizophrenia and exhibits a divergent response to histone deacetylase inhibitors in lymphocyte cultures," J. Psychiatry Neurosci., May 2009, 34(3):232-7.
Geibler et al., "Transcriptional Activators of Human Genes with Programmable DNA-Specificity ," PloS One, 6:e19509 (2011).
GenBank Accesion No. FJ176909.1, "Xanthomonas oryzae pv. oryzae clone 041 avirulence/virulence factor repeat domain protein-like gene, complete sequence," dated Sep. 30, 2008 [retrieved on Aug. 30, 2018]. Retrieved from the Internet: URL <https ://www.ncbi.nlm.nih.gov/nuccore/FJ176909.1/> 2 pages.
GenBank Accession No. NM_001009999.2, "*Homo sapiens* lysine (K)-specific demethylase 1A (KDM1A), transcript variant 1, mRNA," Apr. 6, 2014, 6 pages.
GenBank Accession No. NP_055828.2, "lysine-specific histone demethylase 1A isoform b [*Homo sapiens*]," Apr. 6, 2014, 4 pages.
GenBank Accesssion No. NM_015013.3, "*Homo sapiens* lysine (K)-specific demethylase 1A (KDM1A), transcript variant 2, mRNA," Apr. 6, 2014, 6 pages.
GEO Sample G5M1008573, Duke DnaseSeq HEK293T, Sep. 25, 2012, printed as pages 1/2-282 from https://www.ncbi.nIrn.nih.gov/geo/query/acc.cgi?acc=GSM1008573. 2 pages.
Gillies et al., "A tissue-specific transcription enhancer element is located in the major intron of a rearranged immunoglobulin heavy chain gene," Cell, 33(3):717-728, Jul. 1983.
Gong and Zhu, "Active DNA demethylation by oxidation and repair," Cell Research, 2011, 21:1649-1651.
Gossen and Bujard, "Tight control of gene expression in mammalian cells by tetracycline-responsive promoters," Proc Natl Acad Sci U S A., 89(12):5547-5551, Jun. 15, 1992.
Graef et al., "Proximity and orientation underlie signaling by the non-receptor tyrosine kinase ZAP70," Embo. J., 1997, 16(18):5618-5628.
Greer et al. Histone methylation: a dynamic mark in health, disease and inheritance. Nature Reviews Genetics, vol. 13, pp. 343-357, published online Apr. 3, 2012. (Year: 2012).
Gregory et al., "Selective DNA demethylation by fusion of TOG with a sequence-specific DNA-binding domain", Epigenetics, Apr. 2012, 7(4):344-349.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Gruen et al., "An in vivo selection system for homing endonuclease activity," Nucleic Acids Res., 30(7):e29, Apr. 1, 2002.
Gu et al., "R gene expression induced by a type-III effector triggers disease resistance in rice," Nature, Jun. 23, 2005;435(7045):1122-5.
Guo et el., "Hydroxylation of 5-Methylcytosine by TET1 Promotes Active DNA Demethylation in the Adult Brain ," Cell, 145:423-434 (2011).
Hakimi et al., "A core-BRAF35 complex containing histone deacetylase mediates repression of neuronal-specific genes," Proceedings of the National Academy of Sciences of the United States of America, May 28, 2002, 99(11): 7420-7425.
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
He et al., "Tet-Mediated Formation of 5-Carboxylcytosine and Its Excision by TDG in Mammalian DNA," Science, 333:1303-1307 (2011).
Heintzman et al., "Histone modifications at human enhancers reflect global cell-type-specific gene expression," Nature, 459(7243): 108-112, Epub Mar. 18, 2009.
Heppard et al., "Developmental and Growth Temperature Regulation of Two Different Microsomal [omega]-6 Desaturase Genes in Soybeans," Plant Physiol., 1996, 110:311-319.
Hermonat & Muzyczka, "Use of adeno-associated virus as a mammalian DNA cloning vector: Transduction of neomycin resistance into mammalian tissue culture cells," PNAS, Oct. 1984, 81:6466-70.
Hockemeyer et al., "Genetic engineering of human pluripotent cells using TALE nucleases," Nat. Biotechnol., 29:731-734 (2011).
Hoivik et al., "DNA methylation of intronic enhancers directs tissue-specific expression of steroidogenic factor 1/adrenal 4 binding protein (SF-1/Ad4BP)," Endocrinology, 152(5):2100-2112, Epub Feb. 22, 2011.
Hopp et al., "A Short Polypeptide Marker Sequence Useful for Recombinant Protein Identification and Purification," BioTechnology, Oct. 1988, 6:1204-10.

(56) References Cited

OTHER PUBLICATIONS

Hsu and Zhang, "Dissecting neural function using targeted genome engineering technologies," ACS Chem Neurosci., 3(8):603-610, Epub Jul. 19, 2012.
Huang et al., "Heritable gene targeting in zebrafish using customized TALENs," Nat. Biotechnol., 29:699-700 (2011).
Huang Shi, "Histone methyltransferases, diet nutrients and tumour suppressors," Nature Reviews. Cancer, Jun. 2002, 2(6): 469-7-476.
Humphrey et al., "Stable histone deacety lase complexes distinguished by the presence of SANT domain proteins CoREST/kiaa0071 and Mta-L1," Journal of Biological Chemistry, Mar. 2, 2001, 276(9): 6817-6824.
Inaba et al., "Generation of large numbers of dendritic cells from mouse bone marrow cultures supplemented with granulocyte/macrophage colony-stimulating factor," J Exp Med., 176(6):1693-1702, Dec. 1, 1992.
International Preliminary Report on Patentability in International Application No. PCT/US2012/046451, dated Jan. 21, 2014, 6 pages.
International Preliminary Report on Patentability in International Application No. PCT/US2013/043075, dated Dec. 2, 2014, 7 pages.
International Preliminary Report on Patentability in International Application No. PCT/US2013/064511, dated Apr. 23, 2015, 12 pages.
International Preliminary Report on Patentability in International Application No. PCT/US2014/015343, dated Aug. 20, 2015, 7 pages.
International Search Report and Written Opinion in International Application No. PCT/US2012/046451, dated Nov. 15, 2012, 8 pages.
International Search Report and Written Opinion in International Application No. PCT/US2013/043075, dated Sep. 26, 2013, 10 pages.
International Search Report and Written Opinion in International Application No. PCT/US2013/064511, dated Jan. 30, 2014, 8 pages.
International Search Report and Written Opinion in International Application No. PCT/US2014/015343, dated Jun. 3, 2014, 17 pages.
Isalan et al., "A rapid, generally applicable method to engineer zinc fingers illustrated by targeting the HIV-1 promoter," Nat. Biotechnol., 19(7):656-660, Jul. 2001.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 2009, 8(11):1698-1710.
Jamieson et al., "In vitro selection of zinc fingers with altered DNA-binding specificity," Biochemistry, 33(19):5689-5695, May 17, 1994.
Japanese Office Action in Japanese Application No. 2014-520317, dated Apr. 5, 2016, 8 pages (with English translation).
Jia et al., "Cancer gene therapy targeting cellular apoptosis machinery," Cancer Treatment Reviews, 2012, 38: 868-879.
Jinek et al., "A programmable dual-RNA-guided DNA endonuclease in adaptive bacterial immunity," Science, 337(6096):816-821, Epub Jun. 28, 2012.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases"," Nat. Methods, Jan. 2010, 7:91-92.
Joung et al., "A bacterial two-hybrid selection system for studying protein-DNA and protein-protein interactions," Proc Natl Acad Sci USA, Jun. 20, 2000;97(13):7382-7.
Juillerat et al., "Comprehensive analysis of the specificity of transcription activator-like effector nucleases," Nucleic Acids Res., 42(8):5390-5402, Epub Feb. 24, 2014.

Jumlongras et al., "An evolutionarily conserved enhancer regulates Bmp4 expression in developing incisor and limb bud," PLoS One, 7(6):e38568, Epub Jun. 12, 2012.
Kamijo et al. Tumor spectrum in ARF-deficient mice. Cancer Research, vol. 59, pp. 2217-2222, May 1999. (Year: 1999).
Karmirantzou and Harnodrakas, "A Web-based classification system of DNA-binding protein families," Protein Eng. 14(7):465-472, Jul. 2001.
Kay et al., "A bacterial effector acts as a plant transcription factor and induces a cell size regulator," Science, Oct. 26, 2007;318(5850):648-51.
Kearns et al., "Recombinant adeno-associated virus (AAV-CFTR) vectors do not integrate in a site-specific fashion in an immortalized epithelial cell line," Gene Ther., Sep. 1996, 9:748-55.
Kim et al., "Targeted genome editing in human cells with zinc finger nucleases constructed via modular assembly," Genome Res., 19(7): 1279-1288, Epub May 21, 2009.
Kim et al., "Genome editing with modularly assembled zinc-finger nucleases," Nat. Methods, 7(2):91-92, Feb. 2010.
Kim et al., "Hybrid restriction enzymes: zinc finger fusions to Fok I cleavage domain," Proc Natl Acad Sci USA, Feb. 6, 1996;93(3):1156-60.
Klee et al., "Agrobacterium-Mediated Plant Transformation and its Further Applications to Plant Biology," Ann. Rev. Plant Phys., Jun. 1987, 38:467-486.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Ko et al., "Impaired hydroxylation of 5-methylcytosine in myeloid cancers with mutant TET2," Nature, Dec. 2010, 468(7325):839-843.
Kohn et al., "Engraftment of gene-modified umbilical cord blood cells in neonates with adenosine deaminase deficiency," Nat. Med., 1995, 1:1017-1023.
Koller et al., "Normal development of mice deficient in beta 2M, MHC class I proteins, and CD8+ T cells," Science, Jun. 1990, 248:1227-30.
Kondo et al., "Epigenetic changes in colorectal cancer," Cancer Metastasis Reviews, Jan. 2004, 23(1-2): 29-39.
Ku et al., "Genomewide analysis of PRC1 and PRC2 occupancy identifies two classes of bivalent domains," PLOS Genet., 4(10):e1000242, Epub Oct. 31, 2008.
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lawrence et al., "Supercharging Proteins Can Impart Unusual Resilience," J. Am. Chem. Soc., 2007, 129:10110-10112.
Lea et al., "Aberrant p16 methylation is a biomarker for tobacco exposure in cervical squamous cell carcinogenesis," Am. J. Obstet. Gynecol., 2004, 190:674-9.
Lee et al., "An essential role for CoREST in nucleosomal histone 3 lysine 4 demethylation," Nature, 437(7057):432-435, Epub Aug. 3, 2005.
Lee et al., "Three-dimensional solution structure of a single zinc finger DNA-binding domain," Science., 245(4918):635-637, Aug. 11, 1989.
Li et al. Regulatory mechanisms of tumor suppressor p16AINK4A and their relevance to cancer. Biochemistry, vol. 50, pp. 5566-5582, May 27, 2011.
Li et al., "DNA methylation in prostate cancer," Biochim. Biophys. Acta., Sep. 2004, 1704:87-102.

(56) References Cited

OTHER PUBLICATIONS

Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Transcription activator-like effector hybrids for conditional control and rewiring of chromosomal transgene expression," Sci Rep., 2:897, Epub Nov. 28, 2012.
Li et al., "TAL nucleases (TALNs): hybrid proteins composed of TAL effectors and FokI DNA-cleavage domain," Nucl Acids Res, 39:359-372 (2011).
Lin et al., "iDNA-Prot: identification of DNA binding proteins using random forest with grey model," PLoS One., 6(9):e24756, Epub Sep. 15, 2011.
Lin et al., "Inhibition of Nuclear Translocation of Transcription Factor NF-κB by a Synthetic Peptide Containing a Cell Membrane-permeable Motif and Nuclear Localization Sequence," J. Biol. Chem., 1995, 270:14255-58.
Lippow et al., "Creation of a type IIS restriction endonuclease with a long recognition sequence," Nucleic Acids Res., 37(9):3061-3073, May 2009.
Liu et al., "Regulation of an endogenous locus using a panel of designed zinc finger proteins targeted to accessible chromatin regions. Activation of vascular endothelial growth factor A," J Biol Chem., 276(14):11323-11334, Epub Jan. 5, 2001.
Liu et al., "Validated zinc finger protein designs for all 16 GNN DNA triplet targets," J. Biol. Chem., 277(6):3850-3856, Epub Nov. 28, 2001.
Loenarz and Schofield, Oxygenase Catalyzed 5-Methylcytosine Hydroxylation, Chemistry & Biology, Jun. 2009, 16:580-583.
Lund et al., "DNA Methylation Polymorphisms Precede Any Histological Sign of Atherosclerosis in Mice Lacking Apolipoprotein E," J. Biol. Chem., Jul. 2004, 279:29147-54.
Lutz-Freyerinuth et al., "Quantitative determination that one of two potential RNA-binding domains of the A protein component of the U1 small nuclear ribonucleoprotein complex binds with high affinity to stem-loop II of U1 RNA," PNAS, Aug. 1990, 87:6393-97.
Mabaera et al., "Developmental- and differentiation-specific patterns of human γ- and β-globin promoter DNA methylation," Blood, 110(4):1343-52 (2007).
Madrigal and Krajewski, "Current bioinformatic approaches to identify DNase I hypersensitive sites and genomic footprints from DNase-seq data," Front Genet., 3:230, eCollection 2012, Oct. 31, 2012.
Maeder et al., "Upregulation of the Pluripotency-Associated miRNA 302-367 Cluster 1 Using Engineered Transcription Activator-Like Effector(TALE) Activators," Molecular Therapy, 2012, 20:S193 499.
Maeder et al., "Rapid "open-source" engineering of customized zinc-finger nucleases for highly efficient gene modification," Mol Cell., 31(2):294-301, Jul. 25, 2008.
Maeder et al., "Robust, synergistic regulation of human gene expression using TALE activators," Nat Methods., 10(3):243-245, Epub Feb. 10, 2013.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Maeder et al., "Oligomerized pool engineering (OPEN): an 'open-source' protocol for making customized zinc-finger arrays," Nat Protoc., 2009;4(10):1471-501.
Mahfouz et al., "Targeted transcriptional repression using a chimeric TALE-SRDX repressor protein," Plant Mol Biol., 78(3):311-321, Epub Dec. 14, 2011.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).

Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52 (2008).
Malech et al., "Prolonged production of NADPH oxidase-corrected granulocytes after gene therapy of chronic granulomatous disease," PNAS, Oct. 1997, 94:12133-38.
Mancini et al. "CpG methylation within the 5' regulatory region of the BRCA1 gene is tumor specific and includes a putative CREB binding site," Oncogene, 1998, 16:1161-9.
Mandecki et al., "A totally synthetic plasmid for general cloning, gene expression and mutagenesis in $Escherichia$ $coli$," Gene, Sep. 28, 1990, 94(1):103-107.
Mandell and Barbas et al., "Zinc Finger Tools: custom DNA-binding domains for transcription factors and nucleases," Nucleic Acids Res., 34(Web Server issue): W516-W523, Jul. 1, 2006.
Markmann et al., "Indefinite survival of MHC class I-deficient murine pancreatic islet allografts," Transplantation, Dec. 1992, 54:1085-89.
Martin et al., "GAP domains responsible for ras p21-dependent inhibition of muscarinic atrial K+ channel currents," Science, Jan. 1992, 255:192-194.
Maurano et al., "Systematic localization of common disease-associated variation in regulatory DNA," Science, 337(6099):1190-1195, Epub Sep. 5, 2012.
McDaniell et al., "Heritable individual-specific and allele-specific chromatin signatures in humans," Science, 328(5975):235-239, [author manuscript] Epub Mar. 18, 2010.
McNaughton et al., "Mammalian cell penetration, siRNA transfection, and DNA transfection by supercharged proteins," PNAS, Apr. 2009, 106:6111.
Medenhall et al., "Identification of promoter targets of enhancers by epigenetic knockdown using TAL DNA binding proteins," Epigenetics & Chromatin, 2013, 6(Suppl): 1-2.
Mendenhall et al., "Locus-specific editing of histone modifications at endogenous enhancers," Nat Biotechnol., 31(12):1133-1136, Epub Sep. 8, 2013.
Metzger et al., "LSD1 demethylates repressive histone marks to promote androgen-receptor-dependent transcription," Nature, 437(7057):436-439, 2005.
Miller et al., "A Tale nuclease architecture for efficient genome editing," Nat. Biotechnol., 29(2):143-148, Epub Dec. 22, 2010.
Miller et al., "Repetitive zinc-binding domains in the protein transcription factor IIIA from Xenopus oocytes," Embo J., 4(6):1609-1614, Jun. 1985.
Moore et al., "Design of polyzinc finger peptides with structured linkers," Proc Natl Acad Sci USA, Feb. 2001, 98:1432-1436.
Moore et al., "Improved somatic mutagenesis in zebrafish using transcription activator-like effector nucleases (TALENs)," PLoS One, May 2012, 7(5):e37877.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom TALE-type DNA binding domains by modular cloning," Nucl Acids Res., 39:5790-5799 (2011).
Moscou and Bogdanove, "A simple cipher governs DNA recognition by TAL effectors," Science, 326(5959):1501, Dec. 11, 2009.
Mussolino and Cathomen, "TALE nucleases: tailored genome engineering made easy," Curr Opin Biotechnol., 23(5):644-650, Epub Feb. 17, 2012.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.

(56) References Cited

OTHER PUBLICATIONS

Neering et al., "Transduction of primitive human hematopoietic cells with recombinant adenovirus vectors," Blood, 88(4): 1147-1155, Aug. 15, 1996.
Ng et al., "In vivo epigenomic profiling of germ cells reveals germ cell molecular signatures," Dev Cell., 24(3):324-333, Epub Jan. 24, 2013.
Noonan and McCallion, "Genomics of long-range regulatory elements," Annu Rev Genomics Hum Genet., 11:1-23, 2010.
Novak et al., "Functional Characterization of Protease-treated Bacillus anthracis Protective Antigen," J. Biol. Chem., Aug. 1992, 267:17186-93.
Office Action in Australian Application No. 2017204819, dated Sep. 7, 2018, 7 pages.
Office Action in Australian Application No. 2014214719, dated Feb. 14, 2019, 3 pages.
Office Action in Canadian Application No. 2,841,710, dated Apr. 15, 2019, 4 pages.
Office Action in Canadian Application No. 2,841,710, dated May 11, 2018, 4 pages.
Office Action in European Application No. 12814750.1, dated Mar. 8, 2017, 7 pages.
Office Action in European Application No. 13845212.3, dated Feb. 15, 2018, 4 pages.
Office Action in Japanese Appliaction No. 2014-520317, dated Jan. 17, 2017, 6 pages (with English translation).
Office Action in Japanese Application No. 2015-557129, dated Dec. 19, 2017, 8 pages (with English translation).
Office Action in Japanese Application No. 2017-136828, dated Sep. 11, 2018, 7 pages (with English translation).
Office Action in U.S. Appl. No. 13/838,520, dated Feb. 24, 2017, 49 pages.
Office Action in U.S. Appl. No. 14/435,065, dated Jan. 26, 2017, 22 pages.
Office Action in U.S. Appl. No. 14/435,065, dated Jul. 27, 2017, 25 pages.
Office Action in U.S. Appl. No. 14/766,713, dated Jan. 26, 2017, 39 pages.
Office Action in U.S. Appl. No. 14/766,713, dated Jul. 25, 2017.
Oligino et al., "Drug inducible transgene expression in brain using a herpes simplex virus vector," Gene Ther., 5(4):491-496, Apr. 1998.
Ong and Corees, "Enhancer function: new insights into the regulation of tissue-specific gene expression, " Nat Rev Genet., 12(4):283-293, Epub Mar. 1, 2011.
Orlando et al., "Zinc-finger nuclease-driven targeted integration into mammalian genomes using donors with limited chromosomal homology," Nucleic Acids Res., Aug. 2010;38(15):e152, 15 pages.
Ovchinnikov et al., "PspXI, a novel restriction endonuclease that recognizes the unusual DNA sequence 5-VCTCGAGB-3," Bulletin of Biotechnology and Physico-chemical Biology, 2005, 1(1):18-24.
Paik W K et al., "Enzymatic Demethylation of Calf Thymus Histones," Biochemical and Biophysical Research Communications, 1973, 51(3): 781-788.
Palva et al., "Secretion of interferon by Bacillus subtilis," Gene, 22(2-3):229-235, May-Jun. 1983.
Paques et al., "Meganucleases and DNA double-strand break-induced recombination: persectives for gene thereapy," Current Gene Therapy, Bentham Science Publishers LTD, Feb. 1, 2007, 7(1):49-66.
Partial European Search Report in Application No. 18191841.8, dated Jan. 30, 2019, 17 pages.
Pavletich and Pabo, "Zinc finger-DNA recognition: crystal structure of a Zif268-DNA complex at 2.1 A," Science, 252(5007):809-817, May 10, 1991.
Pekowska et al. H3K4 tri-methylation provides an epigenetic signature of active enhancers. The EMBO Journal, vol. 30, pp. 4198-4210, Aug. 16, 2011, including supplementary figures S1-S11, printed as pages 1/13-13/13.
Perelle et al., "Characterization of Clostridium perfringens Iota-Toxin Genes and Expression in *Eschenichia coli*," Infect. Immun., Dec. 1993, 61:5147-56.
Perez-Pinera et al., "Synergistic and tunable human gene activation by combinations of synthetic transcription factors," Nat Methods., 10(3):239-342, Epub Feb. 3, 2013.
Perez-Quintero et al., "An Improved Method for TAL Effectors DNA-Binding Sites Prediction Reveals Functional Convergence in TAL Repertoires of Xanthomonas oryzae Strains," Jul. 2013, Plos One, 8:e68464 (15 pages).
Pingoud and Silva, "Precision genome surgery," Nat Biotechnol., 25(7):743-744, Jul. 2007.
Porteus & Baltimore, "Chimeric nucleases stimulate gene targeting in human cells," Science. May 2, 2003;300(5620):763.
Prochiantz, "Getting hydrophilic compounds into cells: lessons from homeopeptides," Curr. Opin. Neurobiol., Oct. 1996, 6:629-634.
Qi et al., "Repurposing CRISPR as an RNA-guided platform for sequence-specific control of gene expression," Cell, 152(5):1173-1183, Feb. 28, 2013.
Rada-Iglesias et al., "A unique chromatin signature uncovers early developmental enhancers in humans," Nature, 470(7333):279-283, Epub Dec. 15, 2010.
Ram et al., "Combinatorial patterning of chromatin regulators uncovered by genome-wide location analysis in human cells," Cell, 147(7): 1628-1639, Dec. 23, 2011.
Ramirez et al., "Unexpected failure rates for modular assembly of engineered zinc fingers," Nat Methods., 5(5):374-375, May 2008.
Rebar and Pabo, "Zinc finger phage: affinity selection of fingers with new DNA-binding specificities," Science, 263(5147):671-673, Feb. 4, 1994.
Rendahl et al., "Regulation of gene expression in vivo following transduction by two separate rAAV vectors," Nat. Biotechnol., 16(8):757-761, Aug. 1998.
Reyon et al., "Engineering designer transcription activator-like effector nucleases (TALENs) by REAL or REAL-Fast assembly" Curr Protoc Mol Biol., Chapter 12:Unit 12.15, [author manuscript] Oct. 2012.
Reyon et al., "FLASH assembly of TALENs for high-throughput genome editing," Nat Biotechnol., 30(5):460-465, May 2012.
Rivenbank et al., "Epigenetic reprogramming of cancer cells via targeted DNA methylation," Epigenetics, Apr. 2012, 7(4): 350-360.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Romer et al., "Plant pathogen recognition mediated by promoter activation of the pepper Bs3 resistance gene," Science, Oct. 26, 2007;318(5850):645-8.
Rosenbloom et al., "Encode whole-genome data in the UCSC Genome Browser: update 2012," Nucleic Acids Res., 40(Database issue):D912-D917, Epub Nov. 9, 2011.
Rosenecker et al., "Adenovirus infection in cystic fibrosis patients: implications for the use of adenoviral vectors for gene transfer," Infection, 1996, 24(1)5-8.
Rothman, "Mechanisms of intracellular protein transport," Nature, 372(6501):55-63, Nov. 3, 1994.
Ruben et al., "Isolation of a rel-related human cDNA that potentially encodes the 65-kD subunit of NF-kappa B," Science, Mar. 1991, 251:1490-93.
Sabo et al., "Genome-scale mapping of DNase I sensitivity in vivo using tiling DNA microarrays," Nat Methods., 3(7):511-518, Jul. 2006.
Sabo et al., "Discovery of functional noncoding elements by digital analysis of chromatin structure," Proc Natl Acad Sci U S A., 101(48):16837-16842, Epub Nov. 18, 2004.
Sadowski et al., "GAL4-VP16 is an unusually potent transcriptional activator," Nature, Oct. 1988, 335:563-564.
Samulski et al., "Helper-Free Stocks of Recombinant Adeno-Associated Viruses: Normal Integration Does Not Require Viral Gene Expression," J. Virol., Sep. 1989, 63:3822-28.

(56) References Cited

OTHER PUBLICATIONS

Sander et al., "Targeted gene disruption in somatic zebrafish cells using engineered TALENs," Nat. Biotechnol., 29:697-698 (2011).
Sanjana et al., "A transcription activator-like effector toolbox for genome engineering," Nat Protoc., 7(1):171-192, Jan. 5, 2012.
Schleifman et al., "Triplex-mediated gene modification," Methods Mol. Biol., 435:175-190, 2008.
Schmidt et al., "Arginine-rich cell-penetrating peptides," FEBS Lett., May 2010, 584:1806-13.
Scholze & Boch, "TAL effectors are remote controls for gene activation," J. Curr. Opin. Microbiol, 14:47-53 (2011).
Schonthal, "Regulation of gene expression by serine/threonine protein phosphatases," Semin Cancer Biol., Aug. 1995:6(4):239-48.
Schornack et al., "Gene-for-gene-mediated recognition of nuclear-targeted AvrBs3-like bacterial effector proteins," J Plant Physiol., Feb. 2006; 163(3):256-72.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Sera et al. Zinc-finger-based artificial transcription factors and their applications. Advanced Drug Delivery Reviews, vol. 61, pp. 513-526, Apr. 2009.
Sharma, "Schizophrenia, epigenetics and ligand-activated nuclear receptors: a framework for chromatin therapeutics," Schizophr. Res., Jan. 2005, 72:79-90.
Shi et al., "Histone demethylation mediated by the nuclear amine oxidase homolog LSD1," Cell, 119(7):941-953, Dec. 29, 2004.
Shi et al., "Metabolic enzymes and coenzymes in transcription—a direct link between metabolism and transcription?," Trends in Genetics: TIG, Sep. 2004, 20(9): 445-452.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Sipione et al., "Insulin expressing cells from differentiated embryonic stem cells are not beta cells," Diabetologia, 47(3):499-508. Epub Feb. 14, 2004.
Skinner et al., "Use of the Glu-Glu-Phe C-terminal epitope for rapid purification of the catalytic domain of normal and mutant ras GTPase-activating proteins," J. Biol. Chem., 1991, 266:14163-14166.
Stadler et al., "DNA-binding factors shape the mouse methylome at distal regulatory regions," Nature, 480(7378):490-495, Dec. 14, 2011.
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Stoddard, "Homing endonuclease structure and function," Q. Rev. Biophys., 38(1): 49-95, Epub Dec. 9, 2005.
Stott et al., "The alternative product from the human CDKN2A locus, p14(ARF), participates in a regulatory feedback loop with p53 and MDM2," Embo J., 17(17):5001-5014, Sep. 1, 1998.
Streubel et al., "TAL effector RVD specificities and efficiencies," Nat Biotechnol., 30(7):593-595, Jul. 10, 2012.
Sugio et al., "Two type III effector genes of Xanthomonas oryzae pv. oryzae control the induction of the host genes OsTFIIAgammal and OsTFX1 during bacterial blight of rice," Proc Natl Acad Sci USA, Jun. 19, 2007;104(25):10720-5.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, 324:930-935 (2009).
Tan et al., "Zinc-finger protein-targeted gene regulation: genomewide single-gene specificity," Proc Natl Acad Sci U S A., 100(21):11997-2002, Epub Sep. 26, 2003.
Tani et al., "Updates on current advances in gene therapy," The West Indian Medical Journal, Mar. 2011, 60: 188-194.
Tesson et al., "Knockout rats generated by embryo microinjection of TALENs," Nat. Biotechnol., 29:695-696 (2011).
Thiesen et al., "Conserved KRAB protein domain identified upstream from the zinc finger region of Kox 8," Nucleic Acids Res., 1991, 19:3996.
Thompson et al., "Engineering and Identifying Supercharged Proteins for Macromolecule Delivery into Mammalian Cells," Methods in Enzymology, 2012, 503:293-319.
Thurman et al., "The accessible chromatin landscape of the human genome," Nature, 489(7414):75-82, Sep. 6, 2012.
Tjong and Zhou, "DISPLAR: an accurate method for predicting DNA-binding sites on protein surfaces," Nucleic Acids Res., 35(5): 1465-1477, Epub Feb. 6, 2007.
Topf et al., "Regional 'pro-drug' gene therapy: intravenous administration of an adenoviral vector expressing the E. coli cytosine deaminase gene and systemic administration of 5-fluorocytosine suppresses growth of hepatic metastasis of colon carcinoma," Gene Ther., Apr. 1998, 5:507-513.
Townsend et al., "High-frequency modification of plant genes using engineered zinc-finger nucleases," Nature: International Weekly Journal of Science, Nature Publishing Group, May 21, 2009, pp. 442-445.
Tratschin et al., "A human parvovirus, adeno-associated virus, as a eucaryotic vector: transient expression and encapsidation of the procaryotic gene for chloramphenicol acetyltransferase," Mol. Cell. Biol., Oct. 1984, 4:2072-81.
Tratschin et al., "Adeno-Associated Virus Vector for High-Frequency Integration, Expression, and Rescue of Genes in Mammalian Cells," Mol. Cell. Biol., Nov. 1985, 5:3251-60.
Tremblay et al., "Transcription activator-like effector proteins induce the expression of the frataxin gene," Hum Gene Ther., 23(8):883-890, Epub Jul. 20, 2012.
Uhlman, "An alternative approach in gene synthesis: use of long selfpriming oligodeoxynucleotides for the construction of double-stranded DNA," Gene, Nov. 15, 1988, 71(15): 29-40.
Uhlmann et al., "Distinct methylation profiles of glioma subtypes," Int. J. Cancer, Aug. 2003, 106:52-9.
Urnov et al., "Highly efficient endogenous human gene correction using designed zinc-finger nucleases," Nature, Jun. 2, 2005;435(7042):646-51.
US Final Office Action in U.S. Appl. No. 13/838,520, dated Jul. 15, 2015, 35 pages.
US Non-Final Office Action in U.S. Appl. No. 13/838,520, dated Oct. 6, 2014, 38 pages.
US Non-Final Office Action in U.S. Appl. No. 14/232,067, dated Nov. 17, 2015, 10 pages.
Valton et al., "Overcoming transcription activator-like effector (TALE) DNA binding domain sensitivity to cytosine methylation," J Biol Chem., 287(46):38427-38432, Epub Sep. 26, 2012.
Van den Brulle et al., "A novel solid phase technology for high-throughput gene synthesis," BioTechniques, 45(3):340-343 (2008).
Verma and Weitzman, "Gene Therapy: Twenty-first century medicine," Annual Review of Biochemistry, 2005, 74: 711-738.
Visel et al., "Genomic views of distant-acting enhancers," Nature, 461(7261):199-205, Sep. 10, 2009.
Vogelstein and Kinzler, "Cancer genes and the pathways they control," Nat. Med., Aug. 2004, 10:789-799.
Voytas and Joung, "Plant Science. DNA binding made easy," Science, Dec. 11, 2009, 326:1491-1492.
Wagner et al., "Efficient and persistent gene transfer of AAV-CFTR in maxillary sinus," Lancet, Jun. 1998, 351:1702-1703.

(56) References Cited

OTHER PUBLICATIONS

Wang et al., "An integrated chip for the high-throughput synthesis of transcription activator-like effectors," Angew Chem Int Ed Engl., 51(34):8505-8508, Epub Jul. 23, 2012.
Wang et al., "Human PADA4 regulates histone arginine methylation levels via demethylimination," Science, Oct. 8, 2004, 306(5694): 279-283.
Wang et al., "pH-sensitive immunoliposomes mediate target-cell-specific delivery and controlled expression of a foreign gene in mouse," PNAS, Nov. 1987, 84:7851-7855.
Wang et al., "Positive and negative regulation of gene expression in eukaryotic cells with an inducible transcriptional regulator," Gene Ther., 4(5):432-441, May 1997.
Weber et al., "Assembly of Designer TAL Effectors by Golden Gate Cloning," PloS One, 6:e19722 (2011).
Weising et al., "Foreign Genes in Plants: Transfer, Structure, Expression, and Applications," Ann. Rev. Genet., 1988, 22:421-477.
Welsh et al., "Adenovirus-mediated gene transfer for cystic fibrosis: Part A. Safety of dose and repeat administration in the nasal epithelium. Part B. Clinical efficacy in the maxillary sinus," Hum. Gene Ther., Feb. 1995, 6(2):205-218.
Whyte et al., "Enhancer decommissioning by LSD1 during embryonic stem cell differentiation," Nature, 482(7384):221-225, Feb. 1, 2012.
Widschwendter and Jones, "DNA methylation and breast carcinogenesis," Oncogene, Aug. 2002, 21:5462-82.
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Custom-designed zinc finger nucleases: what is next?" Cell Mol Life Sci., 64(22):2933-2944, Nov. 2007.
Wu, "The 5' ends of *Drosophila* heat shock genes in chromatin are hypersensitive to DNase I," Nature, 286(5776):854-860, Aug. 28, 1980.
Xie et al., "DNA hypomethylation within specific transposable element families associates with tissue-specific enhancer landscape," Nat Genet., 45(7):836-841, Epub May 26, 2013.
Xu et al., "Pioneer factor interactions and unmethylated CpG dinucleotides mark silent tissue-specific enhancers in embryonic stem cells," Proc Natl Acad Sci U S A., 104(30): 12377-12382, Epub Jul. 18, 2007.
Xu et al., "Cytosine methylation targetted to pre-determined sequences," Nat Genet., Dec. 1997;17(4):376-8.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yan et al., "Drugging the undruggable: Transcription therapy for cancer," Biochinnica et Biophysica Acta, 2013, 1835: 76-85.
Yang et al., "Os8N3 is a host disease-susceptibility gene for bacterial blight of rice," Proc Natl Acad Sci USA, Jul. 5, 2006;103(27):10503-8.
Yeager, "Genome Editing in a FLASH ," BioTechniques, Apr. 4, 2012, 2 pages, http://www.biotechniques.com/news/Genome-Editing-in-a-FLASH/biotechniques-329367.html.
Yoon and Brem, "Noncanonical transcript forms in yeast and their regulation during environmental stress," RNA, 16(6):1256-1267, Epub Apr. 26, 2010.
Yost et al., "Targets in epigenetics: inhibiting the methyl writers of the histone code," Curr Chem Genomics, 5(Suppl 1):72-84, Epub Aug. 22, 2011.

Zhang et al., "Efficient construction of sequence-specific TAL effectors for modulating mammalian transcription," Nat Biotechnol., 29(2):149-153, Epub Jan. 19, 2011.
Zhang et al., "Genome-wide identification of regulatory DNA elements and protein-binding footprints using signatures of open chromatin in *Arabidopsis*," Plant Cell., 24(7):2719-2731. Epub Jul. 5, 2012.
Zhang et al., "Programmable Sequence-Specific Transcriptional Regulation of mammilian Genome Using Designer TAL Effectors," Nature Biotechnology, Feb. 2011, 29(2): 149-153.
Zhang et al., "Supplementary Information, Data S1, TET1 is a 5mC hydroxylase in vitro" from, "TET1 is a DNA-binding protein that modulates DNA methylation and gene transcription via hydroxylation of 5-methylcytosine," Cell Res., 6 pages, 2010.
Zhang et al., "Transcription activator-like effector nucleases enable efficient plant genome engineering," Plant Physiol., 161(1):20-27, Epub Nov. 2, 2012.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zheng S et al., "Correlations of partial and extensive methylation at the P14ARF locus with reduced MRNA expression in colorectal cancer cell lines and clinicopathological features in primary tumors," Carcinogenesis, Nov. 1, 2000, 21(11): 2057-2064.
Zitzewitz et al., "Probing the folding mechanism of a leucine zipper peptide by stopped-f1A4:A48ism spectroscopy,"Biochemistry, 34(39):12812-12819, Oct. 3, 1995.
UCSC Genome Browser on Human Dec. 2013 (GRCh38/hg38) Assembly, chr12:5, 432, 047-5, 432, 118, retrieved on Nov. 11, 2021, retrieved from URL <http://genome.ucsc.edu/cgi-bin/hgTracks?db=hg38&lastVirtModeType=default&lastVirtModeExtraState=&virtModeType=default&virtMode=0&nonVirtPosition=&position=chr12%3A5432047%2D5432118&hgsid=1213134839_eQIFaKub3if1WhqtQsuImzsnVEpm>, 2 pages.
Branco et al., "Uncovering the role of 5-hydroxymethylcytosine in the epigenome," Nature Reviews Genetics, Nov. 15, 2011, 13:7-13.
CA Office Action in Canadian Appln. No. 2,900,338, dated Feb. 5, 2021, 5 pages.
EP Extended European Search Report in European Appln. No. 20183740.8, dated Nov. 4, 2020, 15 pages.
EP Extended European Search Report in European Appln. No. 20184257.2, dated Nov. 5, 2020, 13 pages.
EP Extended European Search Report in European Appln. No. 20194689.4, dated Feb. 10, 2021, 8 pages.
EP Office Action in European Appln. No. 18191841.8, dated Apr. 17, 2020, 5 pages.
EP Office Action in European Appln. No. 18191841.8, dated May 10, 2021, 4 pages.
JP Office Action in Japanese Appln. No. 2019-043522, dated Mar. 2, 2021, 7 pages (with English translation).
CA Office Action in Canadian Appln. No. 2,900,338, dated Dec. 16, 2019, 6 pages.
EP Extended European Search Report in EP Appln. No. 19191923.2, dated Feb. 14, 2020, 6 pages.
GenBank Accession No. FJ176909.1, "Xanthomonas oryzae pv. oryzae clone D41 avirulence/virulence factor repeat domain protein-like gene, complete sequence," Sep. 30, 2008, 2 page.
JP Office Action in Japanese Application No. 2017-136828, dated Aug. 27, 2019, 7 pages (with English Translation).
JP Office Action in Japanese Application No. 2018-223519, dated Jan. 7, 2020, 7 pages (with English Translation).
JP Office Action in Japanese Appln. No. 2019-043522, dated Mar. 3, 2020, 8 pages (with English translation).
UCSC Genome Browser (Human Feb. 2009 (GRCh37/hg19) Assembly, chr12:2,162,284-2,162,418 with HEK293T DNase 1 HS track from ENCODE/DUKE, printed from https://genome.ucwsc.edu as p. 1/1 on Jun. 28, 2019. (Year: 2019).

(56) References Cited

OTHER PUBLICATIONS

UCSC Genome Browser (Human Feb. 2009 (GRCh37/hg19) Assembly, chr9:21,440,329-21,440,478 with HEK293T DNase 1 HS track from ENCODE/DUKE, printed from htttps://genome.ucwsc.edu as p. 1/1 on Jun. 25, 2019. (Year: 2019).

* cited by examiner

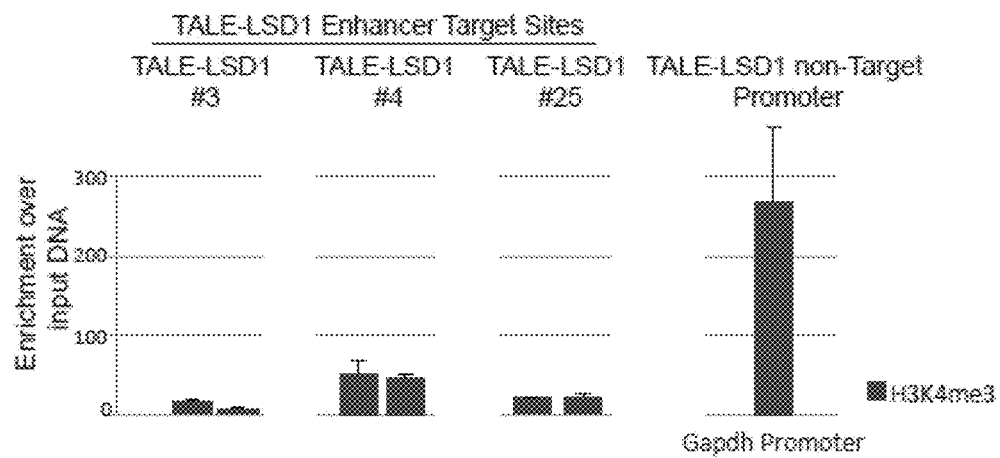
FIG. 4A
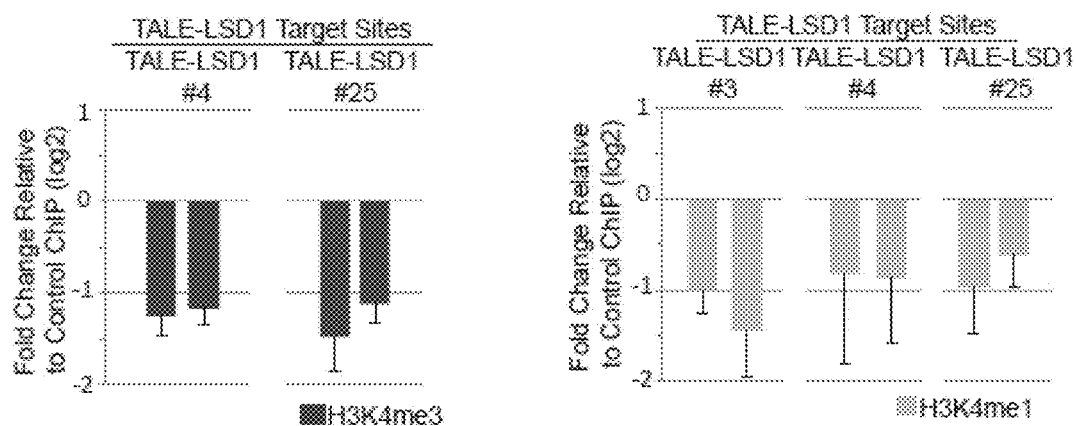
FIGS. 4B-C

TRANSCRIPTION ACTIVATOR-LIKE EFFECTOR (TALE) - LYSINE-SPECIFIC DEMETHYLASE 1 (LSD1) FUSION PROTEINS

CLAIM OF PRIORITY

This application is a continuation of U.S. patent application Ser. No. 14/435,065, filed Apr. 10, 2015, which is a U.S. National Phase Application under 35 U.S.C. § 371 of International Patent Application No. PCT/US2013/064511, filed Oct. 11, 2013, which claims the benefit of, and incorporates by reference, U.S. Provisional Patent Applications Nos. 61/713,098, filed on Oct. 12, 2012; 61/776,039, filed on Mar. 11, 2013, and 61/865,432, filed on Aug. 13, 2013.

FEDERALLY SPONSORED RESEARCH OR DEVELOPMENT

This invention was made with Government support under the National Human Genome Research Institute's ENCODE Project (Grant Nos. U54 HG004570, U54 HG006991) and Grant Nos. DP1 GM105378 and NIH P50 HG005550 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 5, 2019, is named Sequence_Listing.txt and is 66,527 bytes in size.

TECHNICAL FIELD

This invention relates to fusion proteins comprising a DNA binding domain, e.g., a TAL effector repeat array (TALE) or zinc finger, and a catalytic domain comprising a sequence that catalyzes histone demethylation, and methods of use thereof.

BACKGROUND

Mammalian gene regulation is dependent on tissue-specific enhancers that can act across large distances to influence transcriptional activity[1-3]. Mapping experiments have identified hundreds of thousands of putative enhancers whose functionality is supported by cell type-specific chromatin signatures and striking enrichments for disease-associated sequence variants[4-11]. However, these studies do not address the in vivo functions of the putative elements or their chromatin states, and cannot determine which genes, if any, a given enhancer regulates.

SUMMARY

The present invention is based, at least in part, on the development of fusions between transcription activator-like effector (TALE) repeat domains and a histone demethylase, e.g., Lysine-Specific Demethylase 1 (LSD1). As shown herein, these TALE-histone demethylase fusion proteins efficiently remove enhancer-associated chromatin modifications from target loci, without affecting control regions. Inactivation of enhancer chromatin by these fusions frequently causes down-regulation of proximal genes. These 'epigenome editing' tools can be used, e.g., to characterize a critical class of functional genomic elements, or to modulate (e.g., decrease) expression of selected genes).

Thus, provided herein are fusion proteins comprising an engineered DNA-binding domain that binds specifically to a preselected target sequence, and a catalytic domain comprising a sequence that catalyzes histone demethylation.

In another aspect, the invention provides methods for reducing methylation of histones associated with a selected DNA sequence in a mammalian cell. The methods include contacting the cell with a fusion protein comprising an engineered DNA-binding domain that binds specifically to a target sequence, wherein the target sequence is within about 10 kb, 5 kb, 2 kb, or 1 kb, 500 bp, 250 bp, 100 bp, 50 bp, 40 bp, 30 bp, or 20 bp, of the selected DNA sequence, and a catalytic domain comprising a sequence that catalyzes histone demethylation.

In another aspect, the invention provides methods for reducing methylation of histones associated with a selected DNA sequence in a mammalian cell. The methods include contacting the cell with a nucleic acid encoding a fusion protein comprising an engineered DNA-binding domain that binds specifically to a target sequence, wherein the target sequence is within about 10 kb, 5 kb, 2 kb, 1 kb, 500 bp, 250 bp, 100 bp, 50 bp, 40 bp, 30 bp, or 20 bp, of the selected DNA sequence, and a catalytic domain comprising a sequence that catalyzes histone demethylation.

In some embodiments, the fusion proteins comprise a linker between the DNA binding domain and the catalytic domain.

In some embodiments, the DNA-binding domain is or comprises an engineered transcription activator-like (TAL) effector repeat array, zinc finger, triplex-forming oligonucleotide, peptide nucleic acid, or a DNA-binding domain from a homing meganuclease (preferably a catalytically inactive homing meganuclease), or a catalytically inactive Cas9 nuclease.

In some embodiments, the catalytic domain comprises full length LSD1, or a catalytic domain of LSD1, e.g., amino acids 172-833 of the human LSD1 variant 2.

In some embodiments, the fusion proteins comprise a plurality of catalytic domains, optionally with linkers therebetween.

In some embodiments, the cell is a human cell.

In some embodiments, the cell is in a living mammal.

In some embodiments, the selected DNA sequence is a sequence of a p14ARF gene.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

(FIG. 1A) Schematic depicts workflow for identification of nucleosome-free target sequence (black stripe) within enhancer (peaks of histone modification) and design of corresponding TALE fusion. TALE arrays comprising ~18 repeats (ovals) that each bind a single DNA base are fused to the LSD1 histone H3K4 demethylase. (TTACCATGTCTTTCTAAG, SEQ ID NO: 225) Upon transient transfection, we assayed for binding to the target site, induced chromatin changes and altered gene expression. (FIG. 1B) ChIP-seq signal tracks show H3K4me2, H3K27ac and TALE binding in K562 cells across a targeted enhancer in the SCL locus. Control tracks show anti-FLAG ChIP-seq signals in mCherry transfected cells and input chromatin. The target sequence of the TALE is indicated below. (FIG. 1C) ChIP-qPCR data show fold-change of H3K4me2 and H3K27ac enrichment in cells transfected with constructs encoding TALE-LSD1, the same TALE but lacking LSD1, or a 'nontarget' TALE-LSD1 whose cognate sequence is not present in the human genome. Data are presented as log 2 ratios normalized to mCherry plasmid transfected control (error bars represent +s.e.m. n=4 biological replicates). (FIG. 1D) ChIP-seq tracks show H3K4me2 and H3K27ac signals across the target SCL locus for K562 cells transfected with TALE-LSD1 or control mCherry plasmid. (FIG. 1E) ChIP-qPCR to test for off target effects of TALE-LSD1. ChIP-qPCR for H3K4me2 (lighter grey) and H3K27ac (darker grey) at two non-target control enhancers. For comparison, the data from the target enhancer is shown. (FIG. 1F) ChIP-qPCR values for the non-target control TALE-LSD1 (SEQ ID NO: 46). A TALE-LSD1 construct targeting a sequence not present in the human genome was transfected into K562 cells as a control for non-specific effects. Data is shown as ratio of enrichment to mCherry plasmid control for a subset of enhancers shown in FIG. 2. For comparison, an 'on target' TALE-LSD1 construct at its targeted enhancer is shown (TALE-LSD1 #4).

(FIG. 3A) Nine TALE-LSD1 fusions that robustly alter chromatin state (see FIG. 2) were evaluated for their effects on gene expression by RNA-seq (see Methods). For each of the nine fusions, a bar graph shows normalized gene expression values for the closest expressed upstream and downstream genes (error bars represent SEM, n=2 biological replicates). The light and dark grey bars (middle and right bars in each grouping) indicate the mean expression in cells transfected with the corresponding 'on-target' TALE-LSD1 construct, while the black bars (leftmost in each grouping) indicate the mean expression in cells transfected with control 'off-target' TALE constructs (error bars represent standard deviations, * indicates p<0.05). (FIG. 3B) ChIP-seq tracks show H3K4me2 and H3K27ac signals across the Zfpm2 locus. TALE-LSD1 fusions were designed to target candidate enhancers (black bars) in the first intron. (FIG. 3C) Bar graph shows relative ZFPM2 expression in K562 cells transfected with the indicated combinations of TALE-LSD1 constructs. Error bars indicate +s.e.m of 4 RT-qPCR measurements). The data suggest that these enhancers act redundantly in K562 cells to maintain ZFPM2 expression.

FIGS. 4A-4C. ChIP-qPCR to test for effects of TALE-LSD1. (FIG. 4A) ChIP-qPCR enrichment of H3K4me3 for three target enhancers, selected based on prior evidence of H4K4me3 (#4, #25) and one typical enhancer (#3) lacking K4me3. For comparison, data from a H3K4me3 enriched promoter is shown. (FIG. 4B) ChIP-qPCR for H3K4me3 (dark grey) at the two TALE-LSD1 targeted enhancers that showed some H3K4me3 enrichment. The data represent the decrease in enrichment at the target enhancer. (FIG. 4C) ChIP-qPCR enrichment of H3K4me1 for target enhancers of three TALE-LSD1 fusions. The data represent the decrease in enrichment at the target enhancer.

(FIG. 8A) RT-qPCR expression analysis for genes near two TALE-LSD1 target sites. (FIG. 8B) RT-qPCR data showing gene expression for Zfpm2 in cells transfected with a TALE #25 control plasmid that lacks the LSD1 protein, with data from the TALE-LSD1 for comparison. Error bars represent +SEM, n=2 biological replicates.

DETAILED DESCRIPTION

Figure 1A:
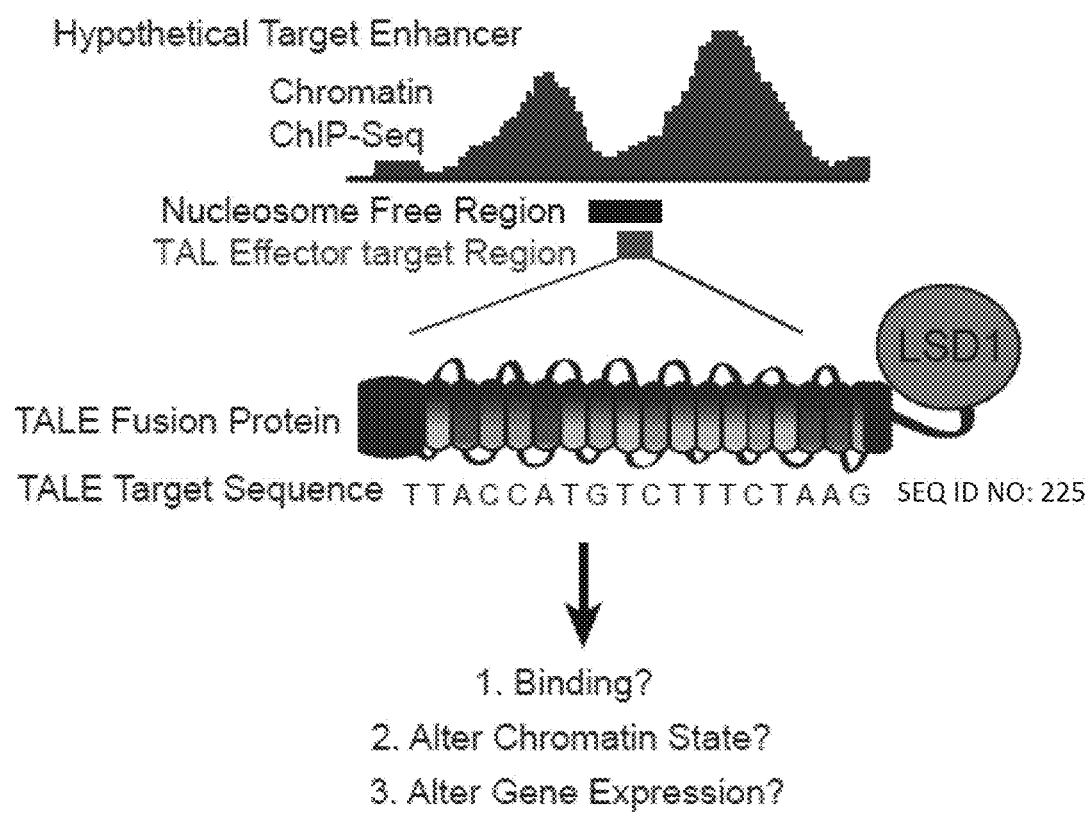
FIGS. 1A-1F. Programmable TALE-LSD1 fusion modulates chromatin at an endogenous enhancer.

Active enhancers are marked by histone H3 K4 mono- and di-methylation (H3K4me1 and H3K4me2) and K27 acetylation (H3K27ac)[4,6,9,12,13]. The present inventors hypothesized that a given enhancer could be inactivated by removal of these chromatin marks. To test this hypothesis, monomeric fusions between TALE repeat arrays and the lysine-specific demethylase 1 (LSD1)[14] were engineered. TALE repeats are modular DNA-binding domains that can be designed to bind essentially any genomic sequence of interest[15,16]. LSD1 catalyzes the removal of H3 K4 and H3 K9 methylation[1-3, 14]. Although prior studies have used TALE nucleases to edit specific genomic regions to disrupt coding sequences[4-11,17,18], it was hypothesized that TALE-LSD1 fusions might provide a more versatile means for modulating the activity of noncoding elements and evaluating the significance of their chromatin states.

Described herein are fusion proteins comprising a DNA-binding domain (i.e., an engineered custom DNA-binding domain), and a catalytic domain (from a different protein) comprising a sequence that catalyzes histone demethylation (e.g., LSD1), with an optional linker between the two domains, such as a linker comprising 2-20, e.g., 10-12, amino acids, preferably a flexible linker (i.e., comprising amino acids such as Glycine and Serine that allow freedom in rotation). An exemplary linker comprises GGSGGSGGS (SEQ ID NO:5). Linkers are known in the art, see, Chen et al., e.g., Adv Drug Deliv Rev. 2012 Sep. 29. pii: S0169-409X(12)00300-6. As described herein, expression of a TAL effector repeat array-LSD1 (TAL-LSD1) fusion protein in human cells results in efficient removal of enhancer-associated chromatin modifications from target loci in close proximity to the target site bound by the TAL effector repeat array part of the protein.

Exemplified is a hybrid protein consisting of an engineered transcription activator-like (TAL) effector repeat array fused to a full length LSD1 protein, e.g., comprising the shorter variant 2 as set forth below, or a truncated form that retains the catalytic function of LSD1, e.g., as described herein. DNA-binding specificity is defined by the engineered TAL effector repeat array. These DNA-binding proteins can be engineered to bind to essentially any DNA sequence and published work from various labs, as well as the inventors' published and unpublished data, has demonstrated that these customizable domains can efficiently target a variety of fused domains to specific genomic locations (Reyon et al., FLASH assembly of TALENs for high-throughput genome editing. Nat Biotechnol (2012).doi: 10.1038/nbt.2170; Moscou and Bogdanove, Science 326, 1501-1501 (2009); Boch et al., Science 326, 1509-1512 (2009); Miller et al., Nat Biotechnol 29, 143-148 (2010)). For example, engineered TAL effector repeat arrays have been fused to the cleavage domain of the FokI endonuclease as well as activators and repressors and act to target these domains to a user-defined sequence within the context of the genome.

DNA-Binding Domains

The fusion proteins described herein can include any DNA Binding Domain (DBD) known in the art or engineered for a specific binding site. Exemplary DBDs include engineered or native TAL effector repeat arrays, engineered or native zinc fingers, modified variants (e.g., catalytically inactive) of homing meganucleases, modified variants (e.g., catalytically inactive) nucleases from the CRISPR-Cas system, chemical nucleases, and other native DBDs.

TAL Effector Repeat Arrays

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., Nature Biotechnology 30, 460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

Widespread adoption and large-scale use of zinc finger protein technology have been hindered by the continued lack of a robust, easy-to-use, and publicly available method for engineering zinc finger arrays. One existing approach, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280; Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

Native DBDs

In some embodiments, a native DBD (e.g., a portion of a wild-type, non-engineered DNA binding protein that binds to a specific target sequence) can be used. For example, the DBD from a transcription factor, nuclease, histone, telomerase, or other DNA binding protein can be used. Typically DBDs include a structure that facilitates specific interaction with a target nucleic acid sequence; common DBD structures include helix-turn-helix; zinc finger; leucine zipper; winged helix; winged helix turn helix; helix-loop-helix; and hmg-box. The native DBD can be from any organism. See, e.g., Kummerfeld & Teichmann, Nucleic Acids Res. 34 (Database issue): D74-81 (2006). The residues in a DNA binding protein that contact DNA, and thus form part of the DBD, can be determined empirically or predicted computationally, e.g., as described in Tjong and Zhou, Nucl. Acids Res. 35:1465-1477 (2007). A database of DNA binding proteins can be used to identify DNA binding proteins and DBDs for use in the present compositions and methods; see, e.g., Harrison, Nature, 353, 715-719 (1991); Karmirantzou and Hamodrakas, Protein Eng. 14(7): 465-472 (2001); Kumar et al., BMC Bioinformatics. 8:463 (2007); Kumar et al., J Biomol Struct Dyn. 26(6):679-86 (2009); Lin et al., PLoS One. 6(9):e24756 (2011).

Where a native DBD is used in a fusion protein described herein, the catalytic domain is from a different protein.

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G, et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010). In some embodiments, catalytically inactive versions of the homing meganucleases are used, e.g., a mutant of I-SceI, e.g., comprising the mutation D44S, wherein the catalytically active aspartate from the first LAGLIDADG motif (SEQ ID NO: 226) is mutated to serine to make the enzyme inactive; N152K, reported to have ~80% of the wt-activity; or the double variant D150C/N152K, which decreases the activity of the enzyme even further, e.g., as described in Gruen et al., Nucleic Acids Res. 2002; 30:e29; Fonfara et al., Nucleic Acids Res. 2012 January; 40(2): 847-860; and Lippow et al., Nucleic Acids Res. 2009 May; 37(9):3061-73.

Nucleases from the CRISPR-Cas System

Catalytically inactive versions of the Cas9 nuclease can also be used as DBDs in the fusion proteins described herein; these fusion proteins are used in combination with a single guide RNA or a crRNA/tracrRNA pair for specificity. A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. The constructs and methods described herein can include the use of any of those Cas9 proteins, and their corresponding guide RNAs or other guide RNAs that are compatible. The Cas9 from *Streptococcus thermophilus* LMD-9 CRISPR1 system has also been shown to function in human cells in Cong et al (Science 339,819 (2013)). Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency. These proteins are preferably mutated such that they retain their ability to be guided by the single guide RNA or a crRNA/tracrRNA pair and thus retain target specificity, but lack nuclease activity.

In some embodiments, the present system utilizes the Cas9 protein from *S. pyogenes*, either as encoded in bacteria or codon-optimized for expression in mammalian cells, containing D10A and H840A mutations to render the nuclease portion of the protein catalytically inactive; see, e.g., Jinek et al., Science 2012; 337:816-821; Qi et al., Cell 152, 1173-1183 (2013).

Chemical Nucleases

DNA binding domains from the so-called "chemical nucleases,"(Pingoud and Silva, Nat Biotechnol. 25:743-4 (2007)), e.g., triplex-forming oligonucleotides or peptide nucleic acids can also be utilized in the present compositions and methods; see, e.g., Schleifman et al., Methods Mol Biol. 2008; 435:175-90; Arimondo et al., Mol Cell Biol. 2006 January; 26(1):324-33; Majumdar et al., J Biol Chem. 2008 Apr. 25; 283(17):11244-52; Simon et al., Nucleic Acids Res. 2008 June; 36(11):3531-8; or Eisenschmidt et al., Nucleic Acids Res. 2005; 33(22):7039-47.

Catalytic Domains

The fusion proteins include a catalytic domain comprising a sequence that catalyzes histone demethylation. Exemplary proteins include the lysine (K)-specific demethylase 1A (KDM1A, also referred to herein as LSD1), a flavin adenine dinucleotide-dependent amino oxidase that catalyzes the removal of H3K4me1 and H3K4me2 (Shi et al., Cell 119: 941-953 (2004); Metzger et al., Nature. 437(7057):436-9 (2005)).

Sequences for human LSD1 are known in the art and are shown in the following table:

| GENBANK ® Accession Nos. | | |
|---|---|---|
| Gene | Nucleic Acid | Amino Acid |
| LSD1-variant 1 | NM_001009999.2 (isoform a) | NP_001009999.1 |
| 1 | mlsgkkaaaa aaaaaaaatg teagpgtagg sengsevaaq paglsgpaev gpgavgertp | |
| 61 | rkkepprasp pgglaeppgs agpqagptvv pgsatpmetg iaetpegrrt srrkrakvey | |
| 121 | remdeslanl sedeyyseee rnakaekekk lpppppqapp eeenesepee psgqagglqd | |
| 181 | dssggygdgq asgvegaafq srlphdrmts qeaacfpdii sgpqqtqkvf lfirnrtlql | |
| 241 | wldnpkiglt featlqqlea pynsdtvlvh rvhsylerhg linfgiykri kplptkktgk | |
| 301 | viiigsgvsg laaarqlqsf gmdvtllear drvggrvatf rkgnyvadlg amvvtglggn | |
| 361 | pmavvskqvn melakikqkc plyeangqad tvkvpkekde mveqefnrll eatsylshql | |
| 421 | dfnvlnnkpv slgqalevvi qlqekhvkde qiehwkkivk tqeelkelln kmvnlkekik | |
| 481 | elhqqykeas evkpprdita eflvkskhrd ltalckeyde laetqgklee klqeleanpp | |
| 541 | sdvylssrdr qildwhfanl efanatplst lslkhwdqdd dfeftgshlt vrngyscvpv | |
| 601 | alaegldikl ntavrqvryt asgceviavn trstsqtfiy kcdavlctlp lgvlkqqppa | |
| 661 | vqfvpplpew ktsavqrmgf gnlnkvvlcf drvfwdpsvn lfghvgstta srgelflfwn | |
| 721 | lykapillal vageaagime nisddvivgr clailkgifg ssavpqpket vvsrwradpw | |
| 781 | argsysyvaa gssgndydlm aqpitpgpsi pgapqpiprl ffagehtirn ypatvhgall | |
| 841 | sglreagria dqflgamytl prqatpgvpa qqspsm (SEQ ID NO: 2) | |
| Gene | Nucleic Acid | Amino Acid |
| LSD1-variant 2* | NM_015013.3 (isoform b) | NP_055828.2 |
| 1 | mlsgkkaaaa aaaaaaaatg teagpgtagg sengsevaaq paglsgpaev gpgavgertp | |
| 61 | rkkepprasp pgglaeppgs agpqagptvv pgsatpmetg iaetpegrrt srrkrakvey | |
| 121 | remdeslanl sedeyyseee rnakaekekk lpppppqapp eeenesepee psgvegaafq | |
| 181 | srlphdrmts qeaacfpdii sgpqqtqkvf lfirnrtlql wldnpkiqlt featlqqlea | |
| 241 | pynsdtvlvh rvhsylerhg linfgiykri kplptkktgk viiigsgvsg laaarqlqsf | |
| 301 | gmdvtllear drvggrvatf rkgnyvadlg amvvtglggn pmavvskqvn melakikqkc | |
| 361 | plyeangqav pkekdemveq efnrlleats ylshqldfnv lnnkpvslgq alevviqlqe | |
| 421 | khvkdeqieh wkkivktqee lkellnkmvn lkekikelhq qykeasevkp prditaeflv | |
| 481 | kskhrdltal ckeydelaet qgkleeklqe leanppsdvy lssrdrqild whfanlefan | |
| 541 | atplstlslk hwdqdddfef tgshltvrng yscvpvalae gldiklntav rqvrytasgc |

-continued

GENBANK® Accession Nos.

```
601    eviavntrst  sqtfiykcda  vlctlplgvl  kqqppavqfv  pplpewktsa  vqrmgfgnln
661    kvvlcfdrvf  wdpsvnlfgh  vgsttasrge  lflfwnlyka  pillalvage  aagimenisd
721    dvivgrclai  lkgifgssav  pqpketvvsr  wradpwargs  ysyvaagssg  ndydlmaqpi
781    tpgpsipgap  qpiprlffag  ehtirnypat  vhgallsglr  eagriadqfl  gamytlprqa
841    tpgvpaqqsp  sm (SEQ ID NO: 1)
```

Variant 2, which was used in the exemplary fusion proteins described herein, lacks two alternate in-frame exons, compared to variant 1. The encoded protein (isoform b) is shorter than isoform a. LSD1 sequences from other species can also be used. See, e.g., FIG. 1 of Chen et al., PNAS Sep. 19, 2006 vol. 103 no. 38 13956-13961. In some embodiments, a fragment of LSD1 corresponding to residues 172-833 of the human LSD1 variant 2 (NP_055828.2) is used (Id.).

Construction of Fusion Proteins

To generate a functional recombinant protein, the DNA binding domain is fused to at least one catalytic domain. Fusing catalytic domains to DBD to form functional fusion proteins involves only routine molecular biology techniques that are commonly practiced by those of skill in the art, see for example, U.S. Pat. Nos. 6,511,808, 6,013,453, 6,007,988, 6,503,717 and U.S. patent application 2002/0160940). Catalytic domains can be associated with the DBD domain at any suitable position, including the C- or N-terminus of the DBD.

In some embodiments, the fusion proteins can include multiple catalytic domains, e.g., on one or both ends of the DBD, e.g., concatenated together with an optional intervening linker; thus there can be one or more catalytic domains on each end of the DBD.

Alternatively, the catalytic domains, e.g., LSD1 units, could be multimerized through specific TALE DBD fused to concatenated protein-protein interaction domains (such as leucine zipper domains or ClonTech's iDimerize system, homodimerization and heterodimerization systems and ligands (e.g. AP20187, AP21967) which were previously provided by ARIAD under the brand name ARGENT. The B/B Homodimerizer (AP20187) induces dimerization of two proteins that each contain the DmrB homodimerization domain. The A/C Heterodimerizer (AP21967) induces dimerization of a protein possessing the DmrA domain and a second protein containing the DmrC domain. The D/D Solubilizer (alternative to AP21998) induces dissociation/disaggregation of proteins possessing DmrD domains. DmrD causes automatic self-association of proteins fused to it; see, e.g., Burnett et al., J. Leukoc. Biol. 75(4):612-623 (2004); Freeman et al., Cancer Res. 63(23):8256-8563 (2003); Castellano et al., Curr. Biol. 9(7): 351-360 (1999); Crabtree and Schreiber, Trends Biochem. Sci. 21(11): 418-422 (1996); Graef et al., Embo. J. 16(18): 5618-5628 (1997); Muthuswamy et al., Mol. Cell. Biol. 19(10): 6845-6857 (1999)). Thus, the catalytic domains fused to a DmrB, DmrA, or DmrD domains could be induced to interact with the TALE DBD in multiple copies. Alternatively, multimerization could be achieved through the use of split-inteins, a class of autocatyltic intein peptides that allow for the seamless covalent splicing of two separate proteins in a predictable and efficient manner (d'Avignon, et al., Biopolymers. 2006 Oct. 15; 83(3):255-67; Zitzewitz, et al., Biochemistry. 1995 Oct. 3; 34(39):12812-9; Li et al., Hum Gene Ther. 2008 September; 19(9):958-64). Both the protein-protein interaction and intein approaches could be optimized to produce very long multimerized strings of catalytic domains. FIGS. 6A-D show exemplary schemes for multimerization.

Methods of Use of the Fusion Proteins

The programmable DBD-LSD1 fusion proteins described herein can be used to modulate the chromatin state and regulatory activity of individual enhancers with high specificity. These reagents are generally useful for evaluating candidate enhancers identified in genomic mapping studies with higher throughput than direct genetic manipulations, particularly when combined with high-throughput methods for engineered TALE-based proteins[24]. Moreover, the fusion proteins can be used to modulate (e.g., decrease) expression of developmental or disease-associated genes in specific contexts by inactivating their tissue-specific enhancers, and thus ultimately yield new therapeutic strategies. In some embodiments, the fusion proteins modulate the activity of an enhancer that only regulates a gene in a very specific context or cell type, rather than simply activating or repressing transcription by directly targeting a promoter. Unlike a promoter that would act in all tissues in which a gene is expressed, genes often have multiple enhancers that switch them on in different cell types or context. Thus the fusion proteins described herein can be designed to target enhancers that regulate the inappropriate expression (or repression) of a particular disease-associated gene in the disease context, and thereby correct the gene in that cell type (but leave it untouched in other cell types). For example, this could be used to regulate a gene that controls immune cell differentiation only in the correct immune cell type, and thus be a very specific way to alter the immune system and correct an autoimmune disorder. For example, BMP4 has tissue specific enhancers that regulate its expression in different tissues; see, e.g., Jumlongras et al., PLoS One. 2012; 7(6): e38568. See also Ong and Corces, Nature Rev. Genetics 12:283-293 (2011). In some embodiments, the gene is described in Xie et al., Nature Genetics 45, 836-841(2013); Gillies et al., Cell 33(3):717-728 (1983); Hoivik et al., Endocrinology. 2011 May; 152(5):2100-12; Xu et al., Proc Natl Acad Sci USA. 104(30): 12377-12382 (2007).

The fusion proteins can be useful for the treatment of disease; for example, the fusion proteins can be targeted to a region of a gene that is overexpressed in a disease state, e.g., as a result of histone hypermethylation. See, e.g., Biancotto et al., Adv Genet. 2010; 70:341-86 (cancer); Dreidax et al., Hum Mol Genet. 2013 May 1; 22(9):1735-45) (p14$^{ARF}$ in neuroblastoma); Copeland et al., Oncogene. 2013 Feb. 21; 32(8):939-46 (cancer); Chase et al., Schizophr Res. 2013 Jun. 28. pii: S0920-9964(13)00321-6 (schizophrenia); and Gavin et al., J Psychiatry Neurosci. 2009 May; 34(3):

232-7 (schizophrenia). Genes that are associated with hypermethylated histones can be identified using methods known in the art, e.g., chromatin immunoprecipitation (see, e.g., Dreidax et al., Hum Mol Genet. 2013 May 1; 22(9):1735-45). In some embodiments, the methods include administering a fusion protein as described herein that comprises a DBD that targets p14$^{ARF}$ for the treatment of cancer, e.g., neuroblastoma.

In some embodiments, e.g., for the treatment of cancer or schizophrenia, a fusion protein as described herein that targets a gene that is underexpressed or overexpressed as a result of histone hypermethylation is administered, optionally in combination with a histone methyltransferase (HMT) inhibitor, e.g., BRD4770 (Methyl-2-benzamido-1-(3-phenylpropyl)-1H-benzo[d]imidazole-5-carboxylate); BIX 01294 (2-(Hexahydro-4-methyl-1H-1,4-diazepin-1-yl)-6,7-dimethoxy-N-[1-(phenylmethyl)-4-piperidinyl]-4-quinazolinamine trihydrochloride hydrate; Chaetocin (from Chaetomium minutum, PubChem Substance ID 24893002); or UNC0224 (7-[3-(dimethylamino)propoxy]-2-(hexahydro-4-methyl-1H-1,4-diazepin-1-yl)-6-methoxy-N-(1-methyl-4-piperidinyl)-4-quinazolinamine). See also Yost et al., Curr Chem Genomics. 2011; 5(Suppl 1):72-84.

The fusion proteins of the present invention are also useful as research tools; for example, in performing either in vivo or in vitro functional genomics studies (see, for example, U.S. Pat. No. 6,503,717, WO 2001019981, and U.S. patent publication 2002/0164575).

Polypeptide Expression Systems

In order to use the fusion proteins described, it may be desirable to express the engineered proteins from a nucleic acid that encodes them. This can be performed in a variety of ways. For example, the nucleic acid encoding the fusion protein can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or for production of the fusion protein. The nucleic acid encoding the fusion protein can also be cloned into an expression vector, for administration to a plant cell, animal cell, preferably a mammalian cell or a human cell, fungal cell, bacterial cell, or protozoan cell.

To obtain expression, the fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered TALE repeat protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of the fusion protein nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein, "MBP." Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in *E. coil*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the fusion protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the DBD domain itself, or another functional domain within the final chimeric protein, has intrinsic nuclear translocation function.

Use of Fusion Proteins in Gene Therapy

The fusion proteins described herein can be used to regulate gene expression or alter gene sequence in gene therapy applications. See for example U.S. Pat. Nos. 6,511,808, 6,013,453, 6,007,988, 6,503,717, U.S. patent application 2002/0164575, and U.S. patent application 2002/0160940. The methods can include administering nucleic acids encoding one or more of the fusion proteins described herein targeted to one or more genes. Since multiple histones across hundreds of basepairs of DNA in promoters or imprinted regions can influence gene expression, it may be desirable to reduce methylation of multiple histones, across longer sequences. If multiple histones, e.g., associated with a larger region of the genome (e.g., a large gene or gene cluster), are desired to be demethylated, a plurality of fusion proteins that target different positions on the same gene or general genomic region, e.g., targeting multiple positions tiled 1000, 500, 300, 250, 100, 50, or 20 bp of the central locus that will target each histone that is to be demethylated, can be administered. Alternatively or in addition, one or a plurality of fusion proteins that are multimerized as described herein can be administered.

Conventional viral and non-viral based gene transfer methods can be used to introduce nucleic acids encoding the fusion protein into mammalian cells or target tissues. Such methods can be used to administer nucleic acids encoding fusion proteins to cells in vitro. Preferably, the nucleic acids encoding the fusion proteins are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, 1992, Science, 256:808-813; Nabel & Felgner, 1993, TIBTECH, 11:211-217; Mitani & Caskey, 1993, TIBTECH, 11:162-166; Dillon, 1993, TIBTECH, 11:167-175; Miller, 1992, Nature, 357:455-460; Van Brunt, 1988, Biotechnology, 6:1149-54; Vigne, 1995, Restorat. Neurol. Neurosci., 8:35-36; Kremer & Perricaudet, 1995, Br. Med. Bull., 51:31-44; Haddada et al., in Current Topics in Microbiology and Immunology Doerfler and Bohm (eds) (1995); and Yu et al., 1994, Gene Ther., 1:13-26.

Methods of non-viral delivery of nucleic acids encoding the fusion proteins include lipofection, microinjection, biolistics, virosomes, liposomes, immunoliposomes, polycation or lipid:nucleic acid conjugates, naked DNA or RNA, artificial virions, and agent-enhanced uptake of DNA or RNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, 1995, Science, 270:404-410; Blaese et al., 1995, Cancer Gene Ther., 2:291-297; Behr et al., 1994, Bioconjugate Chem. 5:382-389; Remy et al., 1994, Bioconjugate Chem., 5:647-654; Gao et al., Gene Ther., 2:710-722; Ahmad et al., 1992, Cancer Res., 52:4817-20; U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding the fusion proteins takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of fusion proteins could include retroviral, lentivirus, adenoviral, adeno-associated, Sendai, and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., 1992, J. Virol., 66:2731-39; Johann et al., 1992, J. Virol., 66:1635-40; Sommerfelt et al., 1990, Virology, 176: 58-59; Wilson et al., 1989, J. Virol., 63:2374-78; Miller et al., 1991, J. Virol., 65:2220-24; WO 94/26877).

In applications where transient expression of the fusion protein is preferred, adenoviral based systems can be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., 1987, Virology 160:38-47; U.S. Pat. No. 4,797,368; WO 93/24641; Kotin, 1994, Hum. Gene Ther., 5:793-801; Muzyczka, 1994, J. Clin. Invest., 94:1351). Construction of recombinant AAV vectors are described in a number of publications, including U.S. Pat. No. 5,173,414; Tratschin et al., 1985, Mol. Cell. Biol. 5:3251-60; Tratschin et al., 1984, Mol. Cell. Biol., 4:2072-81; Hermonat & Muzyczka, 1984, Proc. Natl. Acad. Sci. USA, 81:6466-70; and Samulski et al., 1989, J. Virol., 63:3822-28.

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., 1995, Blood, 85:3048; Kohn et al., 1995, Nat. Med., 1:1017; Malech et al., 1997, Proc. Natl. Acad. Sci. USA, 94:12133-38). PA317/pLASN was the first therapeutic vector used in a gene therapy trial. (Blaese et al., 1995, Science, 270:475-480). Transduction efficiencies of 50% or greater have been observed for MFG-S packaged vectors (Ellem et al., 1997, Immunol Immunother., 44:10-20; Dranoff et al., 1997, Hum. Gene Ther., 1:111-112).

Recombinant adeno-associated virus vectors (rAAV) are a promising alternative gene delivery systems based on the defective and nonpathogenic parvovirus adeno-associated type 2 virus. Typically, the vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., 1998, Lancet, 351:1702-1703; Kearns et al., 1996, Gene Ther., 9:748-55).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., 1998, Hum. Gene Ther. 7:1083-89). Additional examples of the use of adenovirus vectors for gene transfer in clinical trials include Rosenecker et al., 1996, Infection, 24:15-10; Sterman et al., 1998, Hum. Gene Ther., 9:7 1083-89; Welsh et al., 1995, Hum. Gene Ther., 2:205-218; Alvarez et al., 1997, Hum. Gene Ther. 5:597-613; Topf et al., 1998, Gene Ther., 5:507-513; Sterman et al., 1998, Hum. Gene Ther., 7:1083-89.

Packaging cells are used to form virus particles that are capable of infecting a host cell. Such cells include 293 cells, which package adenovirus, and Ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., 1995, Proc. Natl. Acad. Sci. USA, 92:9747-51, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)), followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with nucleic acid (gene or cDNA), encoding the fusion protein, and re-infused back into the subject organism (e.g., patient). Various cell types suitable for ex vivo transfection are well known to those of skill in the art (see, e.g., Freshney et al., Culture of Animal Cells, A Manual of Basic Technique (5th ed. 2005)) and the references cited therein for a discussion of how to isolate and culture cells from patients).

In one embodiment, stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)) are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma and TNF-alpha are known (see Inaba et al., 1992, J. Exp. Med., 176:1693-1702).

Stem cells can be isolated for transduction and differentiation using known methods. For example, stem cells can be isolated from bone marrow cells by panning the bone marrow cells with antibodies which bind unwanted cells, such as CD4+ and CD8+ (T cells), CD45+ (panB cells), GR-1 (granulocytes), and 1ad (differentiated antigen presenting cells) (see Inaba et al., 1992, J. Exp. Med., 176: 1693-1702).

Vectors (e.g., retroviruses, adenoviruses, liposomes, etc.) containing nucleic acids encoding the fusion protein can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Alternatively, stable formulations of the fusion protein can also be administered.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington: The Science and Practice of Pharmacy, 21st ed., 2005).

Delivery Vehicles

An important factor in the administration of polypeptide compounds, such as the fusion proteins of the present invention, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as fusion protein across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, Curr. Opin. Neurobiol., 6:629-634). Another subsequence, the h (hydrophobic) domain of signal peptides, was found to have similar cell membrane translocation characteristics (see, e.g., Lin et al., 1995, J. Biol. Chem., 270:14255-58).

Examples of peptide sequences that can be linked to a protein, for facilitating uptake of the protein into cells, include, but are not limited to: peptide fragments of the tat protein of HIV (Endoh et al., 2010, Methods Mol. Biol., 623:271-281; Schmidt et al., 2010, FEBS Lett., 584:1806-13; Futaki, 2006, Biopolymers, 84:241-249); a 20 residue peptide sequence which corresponds to amino acids 84-103 of the p16 protein (see Fahraeus et al., 1996, Curr. Biol., 6:84); the third helix of the 60-amino acid long homeodomain of Antennapedia (Derossi et al., 1994, J. Biol. Chem., 269:10444); the h region of a signal peptide, such as the Kaposi fibroblast growth factor (K-FGF) h region (Lin et al., supra); the VP22 translocation domain from HSV (Elliot & O'Hare, 1997, Cell, 88:223-233); or supercharged proteins or intraphilins, e.g., as described in US20120100569; US20110112040; Thompson et al,. Methods in Enzymology, 503:293-319 (2012); Cronican et al (2011) Chem Biol. 18, 833; Cronican et al (2010) ACS Chem. Biol. 5, 747; McNaughton et al (2009) Proc. Natl. Acad. Sci. USA 106, 6111; and Lawrence et al (2007) J. Am. Chem. Soc. 129, 10110. See also, e.g., Caron et al., 2001, Mol Ther., 3:310-318; Langel, Cell-Penetrating Peptides: Processes and Applications (CRC Press, Boca Raton FL 2002); El-Andaloussi et al., 2005, Curr. Pharm. Des., 11:3597-3611; and Deshayes et al., 2005, Cell. Mol. Life Sci., 62:1839-49. Other suitable chemical moieties that provide enhanced cellular uptake may also be chemically linked to the Fusion proteins described herein.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), *pertussis* toxin (PT), *Bacillus anthracis* toxin, and *pertussis* adenylate cyclase (CYA), have been used in attempts to deliver peptides to the cell cytosol as internal or amino-terminal fusions (Arora et al., 1993, J. Biol. Chem., 268:3334-41; Perelle et al., 1993, Infect. Immun., 61:5147-56; Stenmark et al., 1991, J. Cell Biol., 113:1025-32; Donnelly et al., 1993, Proc. Natl. Acad. Sci. USA, 90:3530-34; Carbonetti et al., 1995, Abstr. Annu. Meet. Am. Soc. Microbiol. 95:295; Sebo et al., 1995, Infect. Immun., 63:3851-57; Klimpel et al., 1992, Proc. Natl. Acad. Sci. USA, 89:10277-81; and Novak et al., 1992, J. Biol. Chem., 267:17186-93).

Such subsequences can be used to translocate fusion proteins across a cell membrane. The fusion proteins can be conveniently fused to or derivatized with such sequences. Typically, the translocation sequence is provided as part of a fusion protein. Optionally, a linker can be used to link the fusion protein and the translocation sequence. Any suitable linker can be used, e.g., a peptide linker.

The fusion protein can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., the fusion protein.

The liposome fuses with the plasma membrane, thereby releasing the compound into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (e.g., the fusion protein or a nucleic acid encoding the same) at the target tissue or cell. For systemic or tissue specific delivery, this can be accomplished, for example, in a passive manner wherein the liposome bilayer degrades over time through the action of various agents in the body. Alternatively, active compound release involves using an agent to induce a permeability change in the liposome vesicle. Liposome membranes can be constructed so that they become destabilized when the environment becomes acidic near the liposome membrane (see, e.g., Proc. Natl. Acad. Sci. USA, 84:7851 (1987); Biochemistry, 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise the fusion protein and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., 1980, Annu. Rev. Biophys. Bioeng., 9:467, U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication. No. WO 91/17424, Deamer & Bangham, 1976, Biochim. Biophys. Acta, 443:629-634; Fraley, et al., 1979, Proc. Natl. Acad. Sci. USA, 76:3348-52; Hope et al., 1985, Biochim. Biophys. Acta, 812:55-65; Mayer et al., 1986, Biochim. Biophys. Acta, 858:161-168; Williams et al., 1988, Proc. Natl. Acad. Sci. USA, 85:242-246; Liposomes (Ostro (ed.), 1983, Chapter 1); Hope et al., 1986, Chem. Phys. Lip., 40:89; Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., 1990, J. Biol. Chem., 265:16337-42 and Leonetti et al., 1990, Proc. Natl. Acad. Sci. USA, 87:2448-51).

Dosages

For therapeutic applications, the dose of the fusion protein to be administered to a patient can be calculated in a similar way as has been described for zinc finger proteins, see for example U.S. Pat. Nos. 6,511,808, 6,492,117, 6,453,242, U.S. patent application 2002/0164575, and U.S. patent application 2002/0160940. In the context of the present disclosure, the dose should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy, specificity, and $K_D$ of the particular fusion protein employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

Pharmaceutical Compositions and Administration

Appropriate pharmaceutical compositions for administration of the fusion proteins of the present invention can be determined as described for zinc finger proteins, see for example U.S. Pat. Nos. 6,511,808, 6,492,117, 6,453,242, U.S. patent application 2002/0164575, and U.S. patent application 2002/0160940. Fusion proteins, and expression vectors encoding fusion proteins, can be administered directly to the patient for modulation of histone methylation patterns, e.g., and gene expression, and for therapeutic or prophylactic applications, for example, for treatment of diseases listed in associated with histone-mediated inhibition, including cancer (e.g., bladder, brain (e.g., glioma, or glioblastoma), breast, cervical, colon, colorectal, esophagus, head/neck, kidney, leukemia, liver, lung, lymphoma, myeloma, ovary, pancreas, prostate, rhabdomyosarcoma, and uterus cancer); schizophrenia; memory formation; and atherosclerosis. Thus the methods can include identifying a subject who has a disease associated with histone hypermethylation (e.g., optionally including obtaining a sample and detecting methylation of histones, e.g., of histones associated with a disease-associated gene, e.g., $p14^{ARF}$, and selecting the subject if their sample includes hypermethylated histones), and administering a therapeutically effective amount of a fusion protein, or a nucleic acid encoding a fusion protein, as described herein, to the subject.

Administration of therapeutically effective amounts is by any of the routes normally used for introducing fusion proteins into ultimate contact with the tissue to be treated. The fusion proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington: The Science and Practice of Pharmacy, 21st ed., 2005).

The fusion proteins, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

EXAMPLES

The invention is further described in the following examples, which do not limit the scope of the invention described in the claims.
Methods The following materials and methods were used in the examples set forth below.

Construction of TALE fusions. The open reading frame for LSD1 was amplified from a cDNA library from K562 cells using primers (F:gttcaagatctttatctgggaagaaggcgg (SEQ ID NO:3), R:gaccttaattaaatgggcctcttcccttagaa (SEQ ID NO:4)). The PCR product was cloned into a TALE compatible expression vector[27] using PacI and BamHI/BglII such that LSD1 was fused to the C-terminal end of the TALE. TALE repeat array monomers were designed and assembled using FLASH as described[24]. These assembled DNA fragments were cloned into the expression vector using BsmBI sites and verified by restriction enzyme digestion and sequencing. The mCherry control vector was created by incorporating an mCherry open reading frame in place of the TALE array using NotI and PacI. Control TALE vectors lacking LSD1 were constructed using BamHI and PacI to remove LSD1, followed by blunt end ligation. The 3X Flag Tagged TALE vector was created by designing a gBlock (IDT) encoding a 29 amino acid Glycine:Serine linker followed by the 3X Flag sequence and cloning into the BamHI and PacI sites at the C-terminal end of the TALE repeat. Plasmids for construction of LSD1 and 3X Flag fusions will be available from Addgene.

Cell culture and transfection. The human erythroleukemia cell line, K562 (ATCC, CLL-243), was cultured in RPMI with 10% FBS, 1% Pen/Strep (Life Technologies). For transfection, $5 \times 10^6$ cells per transfection were washed once with PBS. Cells were then transfected with 20 ug of TALE plasmid DNA or control mCherry plasmid by nucleofection with Lonza Kit V, as described by the manufacturer (Program T-016). Cells were immediately resuspended in K562 media at a cell density of $0.25 \times 10^6$ cells/ml. Cells were harvested at 72 hours for ChIP or RNA extraction. For ZFPM2 gene expression analysis, the total amount of DNA per transfection was standardized by cotransfecting either 10 ug of a single TALE-LSD1 plasmid plus 10 ug of a scrambled TALE-LSD1 plasmid, or 10 ug each of two TALE-LSD1 plasmids. Transfection efficiency was determine by flow cytometry analysis of mCherry control transfected cells and ranged from 89-94% across multiple biological replicates.

Flag tagged ChIP. TALE-3X Flag transfected K562 cells were crosslinked with 0.5% formaldehyde for 5 minutes at room temperature. Nuclei were isolated and lysed as described[28]. After sonication, solubilized chromatin was incubated with protein G Dynabeads (Invitrogen) and 0.5 ug anti-FLAG M2 antibody (Sigma) at 4° C. overnight. Samples were washed with TBS-T, low salt (150 mM NaCl, 2 mM Tris-HCl, 1% Triton-X), LiCl (250 mM LiCl, 1 mM Tris-HCl, 1% Triton-X), and high salt (750 mM NaCl, 2 mM Tris-HCl, 1% Triton-X) buffers at room temperature. Enriched chromatin was eluted (1% SDS, 5 mM DTT) at 65° C. for 20 minutes, purified and used directly for Illumina library prep. A control library was made from input DNA diluted to 50 picograms. Reads were aligned using Bowtie, and peak analysis was done using MACS with input controls, and masking genomic regions repetitive in Hg19 or K562[29].

Native ChIP. Quantitative measurements of histone modification levels were performed in parallel using native ChIP. 0.01 U of MNase (ThermoScientific) was added to 1 ml lysis buffer (50 mM Tris-HCl, 150 mM NaCl, 1% Triton X-100, 0.1% sodium deoxycholate, 1 mM CaCl2) with EDTA free proteinase inhibitor. For each transfected sample, 260 ul of MNase:Lysis buffer was added and incubated for 15 minutes at 25° C., and 20 minutes at 37° C. MNase was inactivated by adding 20 mM EGTA. The lysed sample was split into 96 well plate format for ChIP with H3K4me2 (abcam ab32356) or H3K27ac (Active Motif 39133). Antibody binding, bead washing, DNA elution and sample clean-up were performed as described[30]. ChIP DNA was analyzed by RT-PCR using FastStart Universal SYBR Green Master (Applied Biosystems), and enrichment ratios were calculated by comparison to equal amount of input DNA. Enrichment was normalized across ChIP samples to two standard off-target control enhancers (Table 2), and fold-ratios were calculated relative to mCherry plasmid transfected cells assayed in parallel. Each TALE ChIP experiment was performed in a minimum of 3 biological replicates. TALE-LSD1 reagents were scored based on the fold-changes of K4me2 and K27ac for two primers flanking the target sequence. A given reagent was scored as 'effective' if it induced a 2-fold or greater reduction in modification signal for at least 2 of these 4 values, with a pvalue<0.05 using a one-tailed t-test. For ChIP-seq maps, 5 ng of ChIP DNA was used for library preparation as described[30].

Gene expression analysis. Genome-wide RNA expression analysis was performed using 3'DGE RNA-seq. Total RNA from 1 million TALE-LSD1 transfected or control (K562 alone or mCherry plasmid transfected) cells in biological replicate using RNeasy Mini kit (Qiagen). 2 ug of total RNA was fragmented and the 3' ends of polyA mRNAs were isolated using Dynabeads (Invitrogen), and used to generate Illumina sequencing libraries, as described[25]. To precisely quantify the gene expression, a 3' DGE analysis pipeline was used. The pipeline estimates gene expression based on the maximum number of reads in any 500 basepair window within 10 kb of the annotated 3' gene end. This approach compensates for the fact that annotated ends for some genes are imprecise and may be cell type dependent and yields accurate quantifications. We then normalized the gene expression levels, scaling samples by the median gene inter-sample variation, as described in[26]. This approach controls for differences in sequencing depth between libraries and in the overall transcript abundance distribution.

The 22 RNA-seq datasets were then normalized based on their negative binomial distributions. Libraries with extreme normalization coefficients below 0.7 or above 1.5 were excluded. To identify candidate regulated genes, the three closest upstream and three closest downstream genes were examined. A gene was specifically scored as regulated if (i) it was detected in control K562 cells with a normalized RNA-seq value>10, i.e. the top $50^{th}$ percentile of expression; (ii) its mean expression value was at least 1.5-fold lower in the corresponding on-target TALE-LSD1 libraries compared to all other libraries, $p<0.05$ calculated using DESeq[26] and (iii) its normalized 3'DGE values in the on-target TALE-LSD1 libraries were the two lowest over all 22 datasets. To simulate the 1000 random binding sites, we sample genomic positions uniformly at random and use rejection sampling to ensure that the random set has a similar distribution relative to genomic annotations (intergenic, promoter, gene body, UTR) to the actual TALE binding sites. We then used significance testing criteria identical to that applied to the actual TALE experiments.

For RT-PCR based expression analysis, total RNA was extracted and reverse transcribed into cDNA using Superscript III First-Strand Synthesis system for RT-PCR (Invitrogen). Quantitative PCR was performed with FastStart Universal SYBR Green Master (Invitrogen) with primer sequences listed in Table 2 on an ABI 7500 machine. Gene expression values are presented as log 2 Ct ratios relative to 2 housekeeping control genes (TBP and SDHA), and represents an average of four independent biological replicates each assayed in two technical replicates.

TABLE 2

Primer Sequences Used

| TALE ID # | ChIP qPCR Primer Set | F | SEQ ID NO: | R | SEQ ID NO: |
|---|---|---|---|---|---|
| 1 | 1.1 | GGAATCGTGAATACCCCTGA | 47 | AACATGCAGGTCTGCTTTCC | 48 |
| 1 | 1.2 | GGAATTGGCCTGCAGAATTA | 49 | GTACACCATTGGCTGGCTCT | 50 |
| 2 | 2.1 | TACTGACCCATGAGCACAGC | 51 | CCCCACTGCCATCCTACTTA | 52 |
| 2 | 2.2 | GAGTGTTGGCAGAATGAGCA | 53 | TGTGCGTATGCATTTTGTTCT | 54 |
| 3 | 3.1 | AGCACACAATTTTGCTCATCA | 55 | ACGTGCACATGGAACAAGAC | 56 |
| 3 | 3.2 | CTGCCAAGTTTCTGGTTGGT | 57 | GAGACAAAATAGCGGGGACA | 58 |
| 4 | 4.1 | AAGAGGACATTCTGGGCTGA | 59 | CCTGCCTCCTAAGCTTCCTT | 60 |
| 4 | 4.2 | GACCTGACTCGAACCCACTC | 61 | GCCTCTGCTAAGGCACAAAC | 62 |
| 5 | 5.1 | TGCCTAGGAAGGCACTTGTC | 63 | GGCTGGAGATCAGCTTTTTG | 64 |
| 5 | 5.1 | TGTCCTGGAACGGTTTCACT | 65 | TTTCTCCTTTGGGCATCTTG | 66 |
| 6 | 6.1 | AAGAGGACATTCTGGGCTGA | 67 | CCTGCCTCCTAAGCTTCCTT | 68 |
| 6 | 6.2 | GACCTGACTCGAACCCACTC | 69 | GCCTCTGCTAAGGCACAAAC | 70 |
| 7 | 7.1 | CCCTTGACCAGGTAGGTTCA | 71 | AAGGAGGGCTCCAGTTTCAT | 72 |
| 7 | 7.2 | TGGTGGAATGAGTAGCAGAGC | 73 | GGGGATTTTCACACTTGGTG | 74 |
| 8 | 8.1 | TGTCTGCACAAATTGCTGTG | 75 | CTTGGGAGGGGTTCAGAGAC | 76 |
| 8 | 8.2 | ACTCAAAGGTGGGTGTGAGG | 77 | TCCGATAATCTGGTCCAAGG | 78 |
| 9 | 9.1 | CCCAGGAAACTTGATGAGAGA | 79 | TGTGGAAGGAGTGAGTGAACA | 80 |
| 9 | 9.2 | GGGTTTTCATGAAGCTTTGAA | 81 | TTTCGTATTGCATCCCATCA | 82 |
| 10 | 10.1 | GCTGAGCTTTTCAGGTAGGC | 83 | GCTCCCAAAAAGATGCAAGT | 84 |
| 10 | 10.2 | GGGCCCTCCTTATACTTGGA | 85 | TGGACTGGGAGGAACATAGC | 86 |
| 11 | 11.1 | TGCTACGTGCAGCGTATTCT | 87 | TGCAACGCTATTTCTCAGGA | 88 |

TABLE 2-continued

Primer Sequences Used

| 11 | 11.2 | AGCATTTTCAGCCTCAGTGG | 89 | CCTTGTAGCACCTCTGTCCA | 90 |
| --- | --- | --- | --- | --- | --- |
| 12 | 12.1 | CAGACTTCTGGAACGCAGTG | 91 | TGTGACAGGCCAAGTCTCAG | 92 |
| 12 | 12.2 | CTGACGGTTTATGAGCAGCA | 93 | GTTTCCCACAGTTCCCTGAA | 94 |
| 13 | 13.1 | TGAAGTCCACATGTTTAGCTCCT | 95 | TGGAAGGAATGTGATTCCACT | 96 |
| 13 | 13.2 | TTCAACAGCAACCAGGAATG | 97 | AAGCTCAAAAAGAAAAACTTCAACA | 98 |
| 14 | 14.1 | CCATTTTCCGTACATGGTGA | 99 | CTGGCTGTAGGGCTCTGTTC | 100 |
| 14 | 14.2 | GACGGGGAAGGAAGAAAGAA | 101 | TCCCAGCTCTCGCAGCTT | 102 |
| 15 | 15.1 | TACACAACAGCACCCACACA | 103 | CCCCATTTCAGTTCTTTCTCA | 104 |
| 15 | 15.2 | TCTTCTGGGTTTGTTGGCTA | 105 | GGCACCATGTGAACTCTCCT | 106 |
| 16 | 16.1 | TCCAACTCAATGCCTTTTCTG | 107 | CACAGGCAAGATTCCCATTT | 108 |
| 16 | 16.2 | AATGGCTCTGGAGAAAAGCA | 109 | GCATGCCAGTCTGAAGATGA | 110 |
| 17 | 17.1 | TGTGAACCTCGAGAAGTGTGA | 111 | TTGTTGAGGTGTGCATGAGG | 112 |
| 17 | 17.2 | GTCATGTCCAGCAGGATGC | 113 | ATGCAGCTGACCCATTGTTT | 114 |
| 18 | 18.1 | ACGATGGAGGACATTGGAAG | 115 | TGAAGGCTTTTCAGGAGCTT | 116 |
| 18 | 18.2 | CTGCAAACAAGGTCTTTGGAC | 117 | AGGCAGCTACCTGGTTAAGG | 118 |
| 19 | 19.1 | GTGACCTTGGAGACGTTGCT | 119 | AGCCTCTTGAACCAGAGCAG | 120 |
| 19 | 19.2 | AAGAGAAGGAGAACCAAGCCTTA | 121 | CACACCAGCAAAGAGCAAAA | 122 |
| 20 | 20.1 | GATTCCGGGTCACTGTGAGT | 123 | TTTTACGGCGAGATGGTTTC | 124 |
| 21 | 21.1 | GGAAGAAAGGAAGGTAGGAAGG | 125 | AGGGCACTCTCCTCTCCTCT | 126 |
| 21 | 21.2 | GCTGAGACCACCCACTCTTC | 127 | CCCAGAAGGAATTACCCACA | 128 |
| 22 | 22.1 | TCACACATCACTTGCGTTCA | 129 | TGGCTTGATAACCCAACCAT | 130 |
| 22 | 22.2 | AGGGAGCACTCTAGGGATGG | 131 | CAGGGGAAACAGGAAGTGAG | 132 |
| 23 | 23.1 | CCACTAAACCGCAACCAAAG | 133 | GGAAACTCCCAGCTTTCAAAC | 134 |
| 23 | 23.2 | CGTTTCTCCCTGGGTTCTTT | 135 | ATTTTTCTGCCTCCCAAACC | 136 |
| 24 | 24.1 | CTGCCCCAAAGAAAGGTAT | 137 | TTGGCATACTTCATGCTCACA | 138 |
| 24 | 24.2 | TTGACATTAGGTCCAGGTTTGA | 139 | TATTTTAGGGCAGGCACACC | 140 |
| 25 | 25.1 | TCATTTTGGTAGCCTTTCTGC | 141 | CACTCAAGTCCCAGGTTGGT | 142 |
| 25 | 25.2 | GATGATTTGGCTTTTGCGATA | 143 | CTTGTGGGAGCTCGACATTA | 144 |
| 26 | 26.1 | GACGTGTTGGTGCATACCTG | 145 | ATGAGGCTCCTCCCTCATTT | 146 |
| 26 | 26.2 | TCAAGAGTACGGCAATCACG | 147 | GGGAAACCGAAGGATTGATT | 148 |
| 27 | 27.1 | GACCACCGGTCTTCTCATGT | 149 | GCAGCTGATGAAGAGCAGAA | 150 |
| 27 | 27.2 | TAGGGTGTGGATGTGGAACA | 151 | TGGGAAATTGCTGTGTTGAG | 152 |
| 28 | 28.1 | TCCTGTAAAGTCCTCAGATCAACA | 153 | GCCAGCTTCTAAGGATGCAC | 154 |
| 28 | 28.2 | TTGGTCTTTGGCCTTCTAGG | 155 | AATGGGAAGTGACAAGGAA | 156 |
| 29 | 29.1 | CAGCCTTTCTAGGAATCACAAA | 157 | GGATGATGAGGAACTGGCTTT | 158 |
| 30 | 30.1 | GTGAACCACCAAGCACAGC | 159 | AGCAGGGGTGGAGAGAAAT | 160 |
| 30 | 30.2 | GGCTACAGCGTCTTCCTGTG | 161 | CACACACCACACCCACAACT | 162 |
| 31 | 31.1 | TAAGGCCGGTCTATCACAGC | 163 | GCAGTCTCAGCACCTCAACC | 164 |
| 31 | 31.2 | ACTGCCTGCCTGGAGTCTAC | 165 | TCGCTCACTGAGGAATGATG | 166 |

TABLE 2-continued

Primer Sequences Used

| | | | | | |
|---|---|---|---|---|---|
| 32 | 32.1 | TACACCGCGAAGGGATAGTC | 167 | TGGGGGTCAGAGAGAGAATG | 168 |
| 33 | 33.1 | GGGCCCCAGACTTTAATTTG | 169 | GCCTCTGGAGTGCAGTACCT | 170 |
| 33 | 33.2 | CCCAGATATTTCCTGCTCCA | 171 | CCCCCAAATTCCATTATTCC | 172 |
| 34 | 34.1 | GAGGGAGCGAGCCATAGTG | 173 | ACAATGGGGCTGCCTGAG | 174 |
| 34 | 34.2 | GGAGGAGGGTGGTCTCTCAT | 175 | TCGAAAGCTACACGGCTCTT | 176 |
| 35 | 35.1 | TGGGTGAGGAAGGAGAAAGA | 177 | AAACCCCTATGGGCAACTCT | 178 |
| 36 | 36.1 | CTGGCCCTCTTCTCCTTTCT | 179 | CAATCATTTGCCAACACAGG | 180 |
| 36 | 36.2 | GTCTGAGGAAAGGCACCTGA | 181 | TCGCACCTGTGTGAGAGGTA | 182 |
| 37 | 37.1 | AGCGACAAAAGGTCAACAGA | 183 | GGTGTTGCGGAAAACACTTT | 184 |
| 37 | 37.2 | CCTAAGAATCAGAAACGCAATG | 185 | CAGTCTGGGCAACAGAACAA | 186 |
| 38 | 38.1 | AACGAAACACAACCTGCACA | 187 | CTGTAACCCTACCCCCAACC | 188 |
| 38 | 38.2 | CAGAACAAAATGGAGTCTTAGCC | 189 | TCAGAAGGTGTGGGGAAAAG | 190 |
| 39 | 39.1 | ATGGCTTTCATGAAGCTGGA | 191 | CGTCTGTGCGAAGAGAAGC | 192 |
| 39 | 39.2 | AAAGCATTTTTGCCATCCAG | 193 | TTCCCGGTTAGATGAGTTGG | 194 |
| 40 | 40.1 | GCCCTCCCTTGATAAGAACC | 195 | TGGGAACCTCTCCATCTCAC | 196 |
| 40 | 40.1 | CCAAAGTCACATGGATGACAG | 197 | GGCTAAATGAGGCAGATGCT | 198 |

| TALE ID # | cDNA qPCR Primer Set | F | | R | |
|---|---|---|---|---|---|
| 14 | GPKOW | CTGAGGGAAGACATGCTGGA | 199 | AGTGAAGCTCCACCACCTGA | 200 |
| | MAGIX | CCCAGCTCCACCTGGTTATT | 201 | CTAGGGAAGTGCTGCTGCTG | 202 |
| | PLP2 | ATGTGTGACCTGCACACCAA | 203 | CTTTACCCCTGCGACGATTT | 204 |
| | PRICKLE3 | GGCACCAGCACAGAGTTAGC | 205 | GACGACCGAAGGCACTATCA | 206 |
| 25 | LRP12 | GAAGCTCCTCCCTCGTATGG | 207 | TCCAAGCTGAGATCGTACCG | 208 |
| | ZFPM2.1 | ATCAGATTTCCAGCCTGTGC | 209 | TGATCACGGAATCAGCAGTG | 210 |
| | ANGPT1 | CTGGGACAGCAGGAAAACAG | 211 | TAGATTGGAGGGGCCACAAG | 212 |
| | ZFPM2.2 | GGCCTGAAAATCTGAGCTGC | 213 | CAGTCGTCTGTCTCAACTCCA | 214 |
| | ZFPM2.3 | GTACAGCAAAGGGGGTCAGC | 215 | GACTGGCAGCTTGTAGCCTT | 216 |
| | ZFPM2.4 | GTTTTATCTTTTGAAAGGCACAGTC | 217 | TTGTGATCACCAGGTGCAGT | 218 |
| | ZFPM2.5 | TCAATTCAGCTGCTTCCTCA | 219 | CTGGAAATCTGATGGGCACT | 220 |
| | SDHA | TCTGCACTCTGGGGAAGAAG | 221 | CAAGAATGAAGCAAGGGACA | 222 |
| | TBP | TTCCCCATGAACCACAGTTT | 223 | TGCAATACTGGAGAGGTGGA | 224 |

Example 1

Figure 1B:
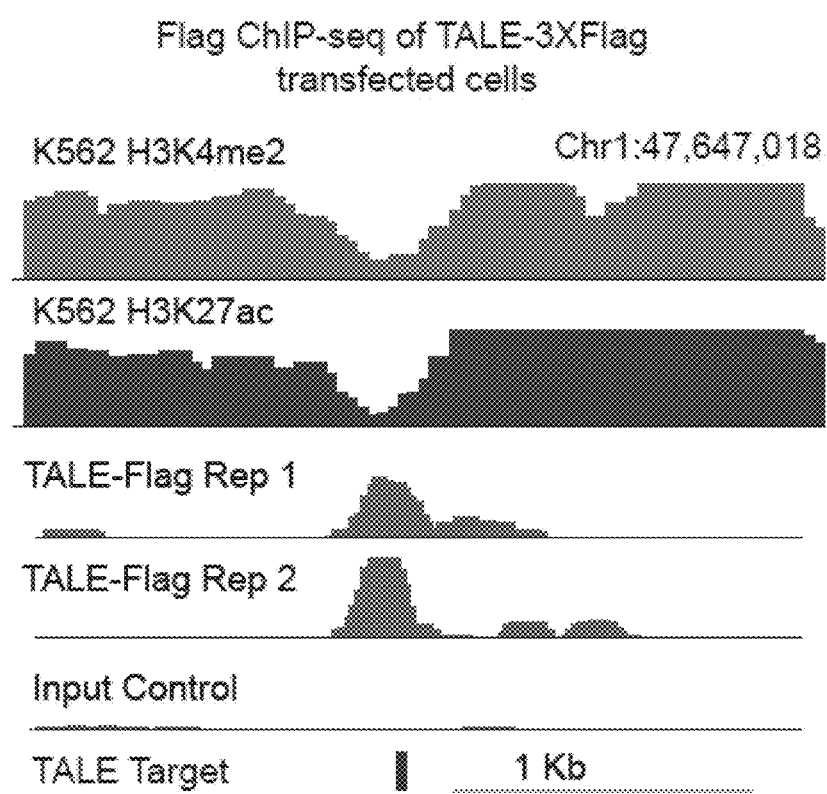

Initial experiments focused on a candidate enhancer in the stem cell leukemia (SCL) locus that is enriched for H3K4me2 and H3K27ac in K562 erythroleukemia cells[4,6,9,12,13,19]. SCL encodes a developmental transcription factor with critical functions in hematopoiesis that is expressed in K562 cells. A TALE array was designed to bind an 18 base sequence in a segment of this enhancer predicted to be nucleosome-free based on DNase hypersensitivity (FIG. 1A). Since the binding specificity of monomeric TALEs has yet to be thoroughly characterized, an expression construct encoding this TALE array fused to a 3X FLAG epitope was first created. This construct was transfected into K562 cells, expression confirmed by Western blot, and genome-wide binding mapped by chromatin immunoprecipitation and sequencing (ChIP-seq). The top ranked binding site corresponded precisely to the target sequence within the SCL locus (FIG. 1B, Table 3). No other ChIP-seq peaks were reproducibly detected in the two biological replicates.

TABLE 3

TALE-3X Flag ChIP-seq Peaks

| Chr location | Rep1 tags | Rep2 tags | pvalue |
|---|---|---|---|
| chr1: 47,646,591-47,647,590 | 25 | 20 | 0.01 |
| chr1: 17,221,975-17,222,974 | 3 | 8 | 0.14 |
| chr5: 78,850,956-78,851,955 | 5 | 1 | 0.21 |
| chr17: 51,183,234-51,184,233 | 2 | 4 | 0.15 |

Peak calls using MACS in two biologically independent replicates along with reads falling within a 1 kb window around the peak. Grey shading indicates the target locus. P-values calculated by comparison of both biological replicates to the input control library.

The genome was scanned for sequence motifs with one or two mismatches from the TALE recognition motif, but no significant ChIP-seq enrichments were detected at these sites either (Table 4).

TABLE 4

| Target Sequence | TALE-3X Flag ChIP tags per 1 kb bin | Input tags per 1 kb bin |
|---|---|---|
| 18/18 Target (n = 1) | 17.5 | 1 |
| 17/18 Targets (n = 2) | 0.5 | 0.5 |
| 16/18 Targets (n = 52) | 0.40 | 0.58 |

The sequence read count at 54 genomic loci with 1 or 2 mismatches compared to the perfect match target locus for the TALE-3X Flag.

These data support the specificity of TALE binding and are consistent with prior demonstrations of TALE activator domain fusions that selectively induce target genes[14,18,20].

Example 2

To modulate chromatin state at the SCL enhancer, the corresponding TALE was combined with the LSD1 demethylase. K562 cells were transfected with a construct encoding this TALE-LSD1 fusion or a control mCherry vector, the cells cultured for three days and histone modification levels measured by ChIPqPCR.

Figure 1C:
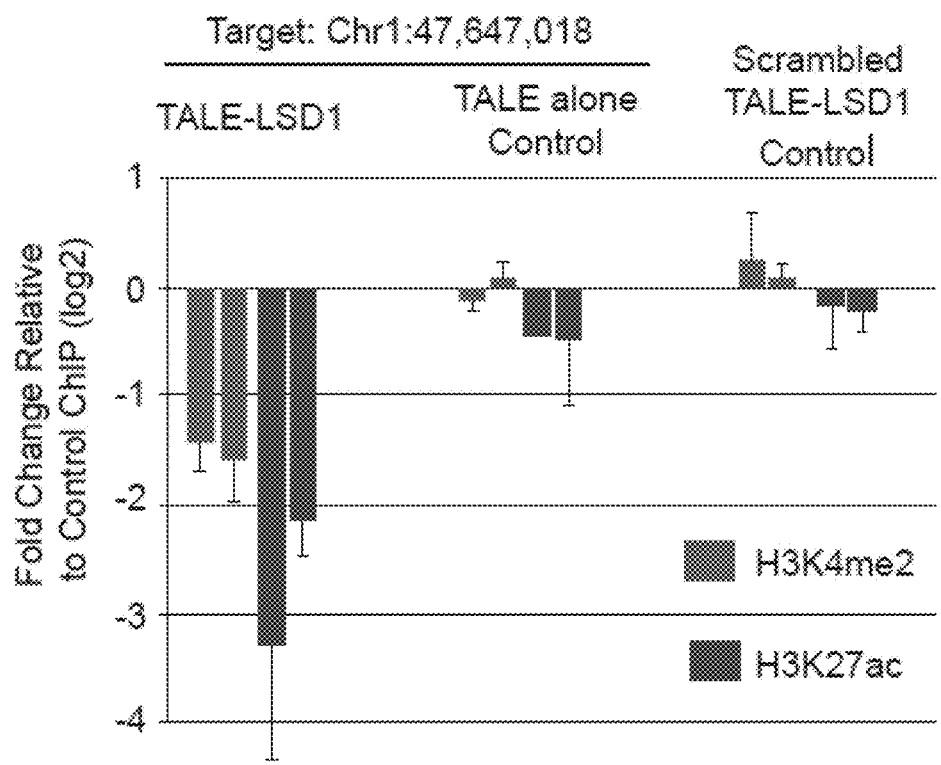
Figure 1D:
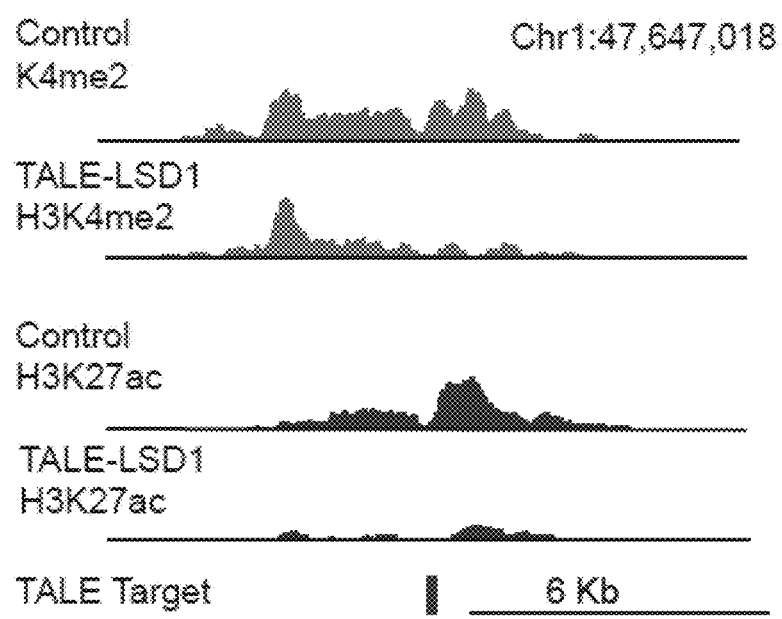
Figure 1E:
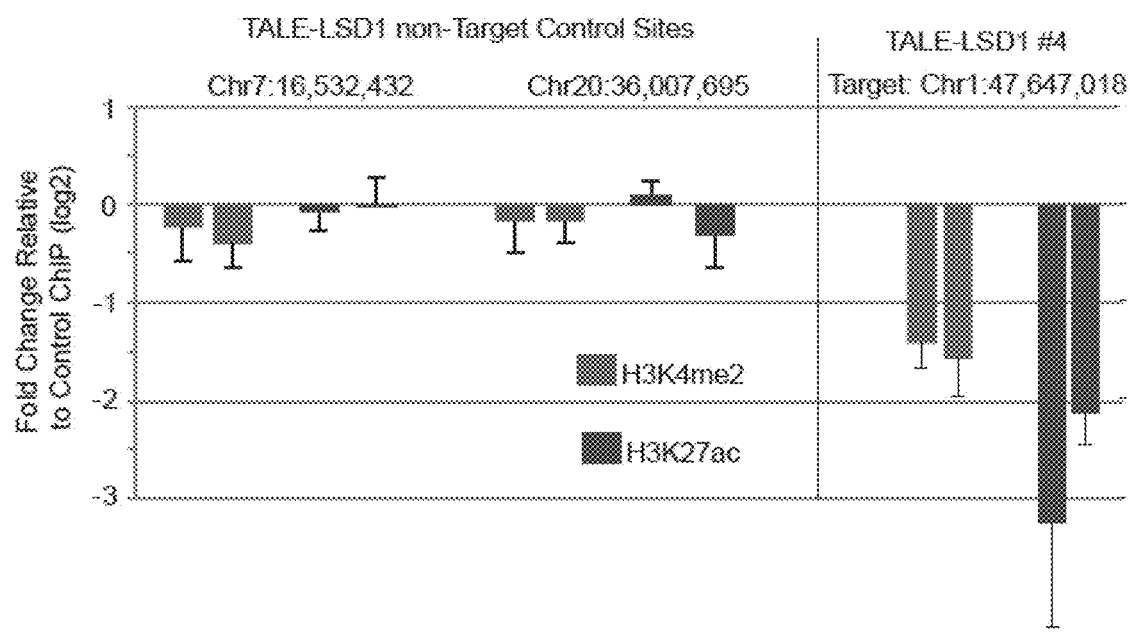

The fusion reduced H3K4me2 signals at the target locus by ~3-fold relative to control, but had no effect at several non-target control enhancers (FIGS. 1C and 1E). In addition to its enzymatic activity, LSD1 physically interacts with other chromatin modifying enzymes, including histone deacetylases[21]. Therefore changes in H3K27ac, another characteristic enhancer mark, were also assayed. The fusion reduced H3K27ac levels by >4-fold, suggesting that LSD1 recruitment leads to generalized chromatin inactivation at the target enhancer.

Example 3

Figure 1F:
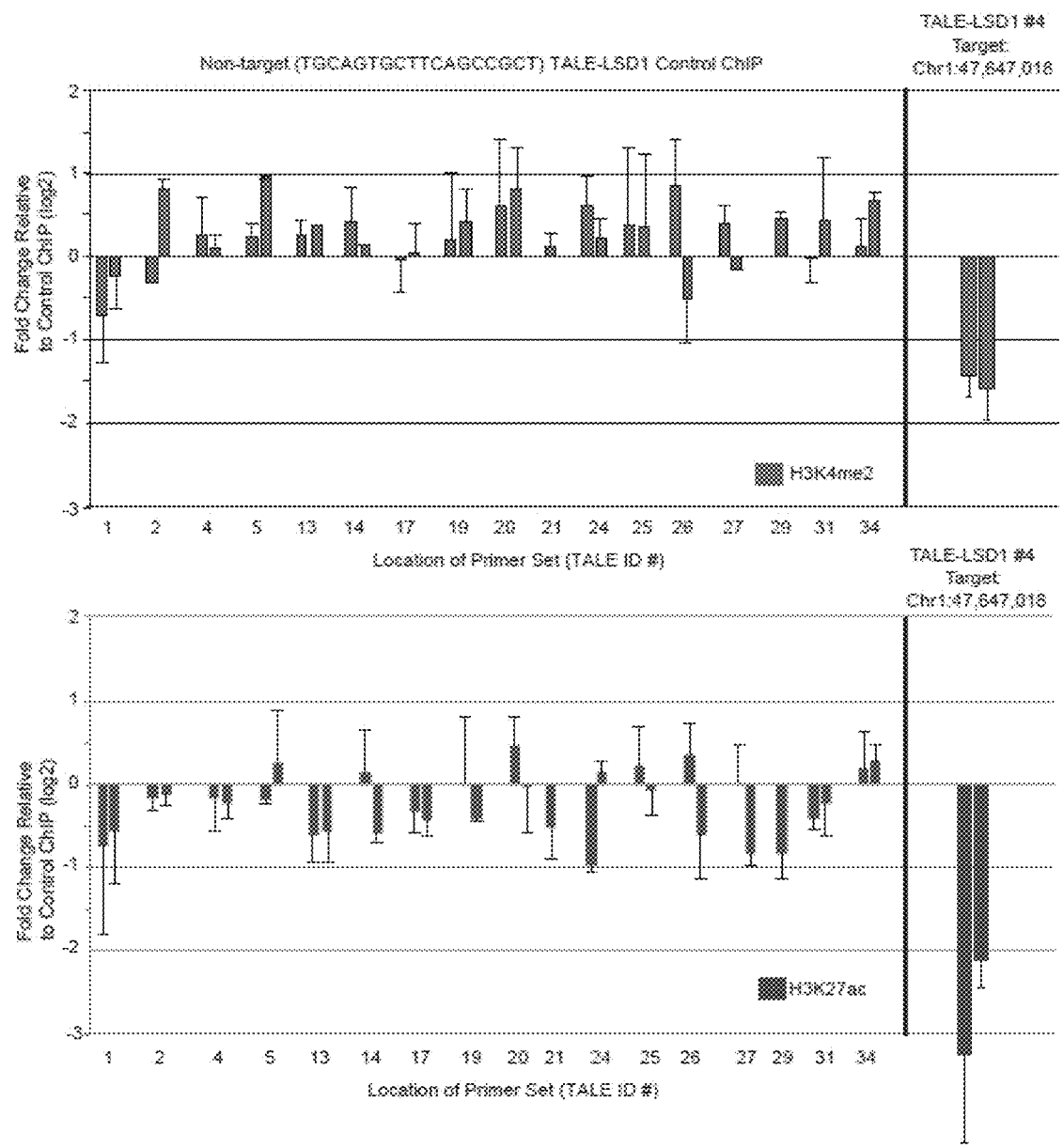

To eliminate the possibility that the chromatin changes reflect displacement of other transcription factors by the TALE, a construct encoding the TALE without LSD1 was tested. A TALE-LSD1 fusion with a scrambled target sequence not present in the human genome was also examined to control for non-specific effects of LSD1 overexpression. Neither construct altered H3K4me2 or H3K27ac levels at the SCL locus (FIGS. 1C and 1F).

Lastly, to evaluate the specificity of the fusion comprehensively, ChIP-seq was used to map H3K4me2 and H3K27ac genome-wide in TALE-LSD1 and control transfected K562 cells. These data confirmed loss of H3K4me2 and H3K27ac across a 2 kb region surrounding the target sequence within the SCL locus (FIG. 1D).

These results indicate that directed LSD1 recruitment results in locus-specific reduction of H3K4me2 and H3K27ac. The generalized effect on chromatin state may be a direct consequence of H3K4 demethylation or, alternatively, may depend on partner proteins that associate with LSD1[15,16,22,23]. Regardless, prior studies indicate that sequence elements enriched for H3K4me2 and H3K27ac exhibit enhancer activity in corresponding cell types, while elements lacking these marks are rarely active[4,6,12]. Hence, these results suggest that this TALE-LSD1 fusion efficiently and selectively inactivates its target enhancer.

Example 4

The study was expanded to investigate a larger set of candidate enhancers with active chromatin in K562 cells. These include nine elements in developmental loci, sixteen additional highly cell type-specific elements, and fifteen intergenic elements. TALE repeat arrays were designed and produced for sequences in these 40 enhancers using the Fast Ligation-based Automatable Solid-phase High-throughput (FLASH) assembly method[24] (Table 1). LSD1 fusion constructs were then cloned for each TALE and transfected individually into K562 cells, alongside mCherry control plasmid transfected separately into cells. At three days post transfection, H3K4me2 and H3K27ac were measured by ChIPqPCR using two primer sets per target enhancer.

Figure 2:
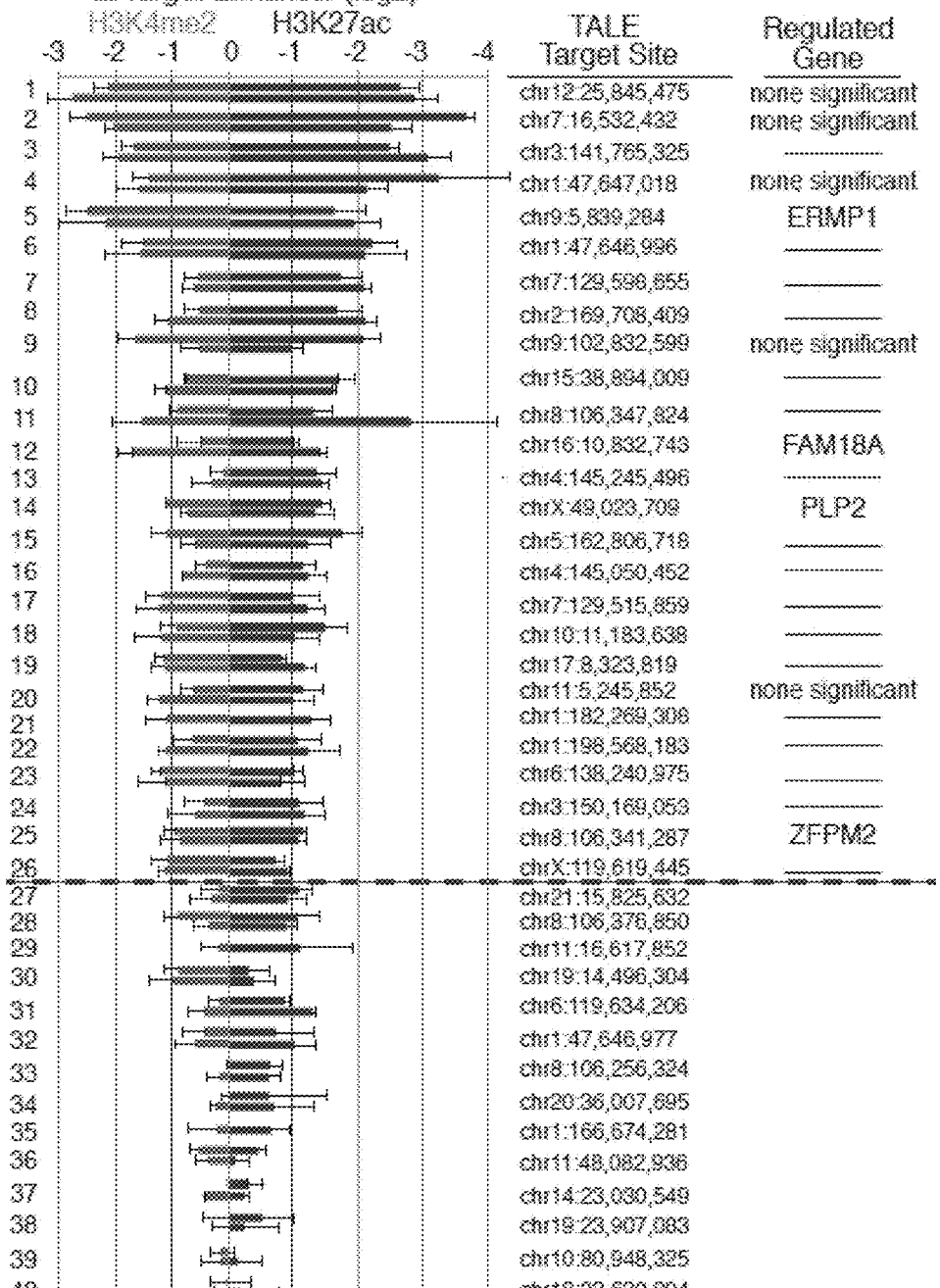
FIG. 2. TALE-LSD1 fusions targeting 40 candidate enhancers in K562 cells. The FLASH assembly method was used to engineer 40 TALE-LSD1 fusions that recognize 17-20 base sequences in nucleosome-free regions of candidate enhancers. These reagents were transfected into K562 cells and evaluated by ChIP-qPCR. Bi-directional plot shows fold change of H3K4me2 (lighter grey, left) and H3K27ac (darker grey, right) at the target locus for each of the 40 fusions, which are ordered by strength of effect and labeled by their target genomic site. Most target sites were evaluated using two qPCR primer sets. Data are presented as log 2 ratios normalized to mCherry plasmid transfected control (error bars represent +s.e.m., n=3 biological replicates). The solid lines (indicated at the bottom by arrows) define a 2-fold difference (log 2=−1). The horizontal dashed line demarcates constructs that induce a 2-fold reduction in histone modification levels for two or more of the four values shown. Regulated genes for 9 tested fusions are shown at right (see Examples and FIGS. 3A-3C). The data indicate that TALE-LSD1 reagents provide a general means for modulating chromatin state at endogenous enhancers.
Figure 5:
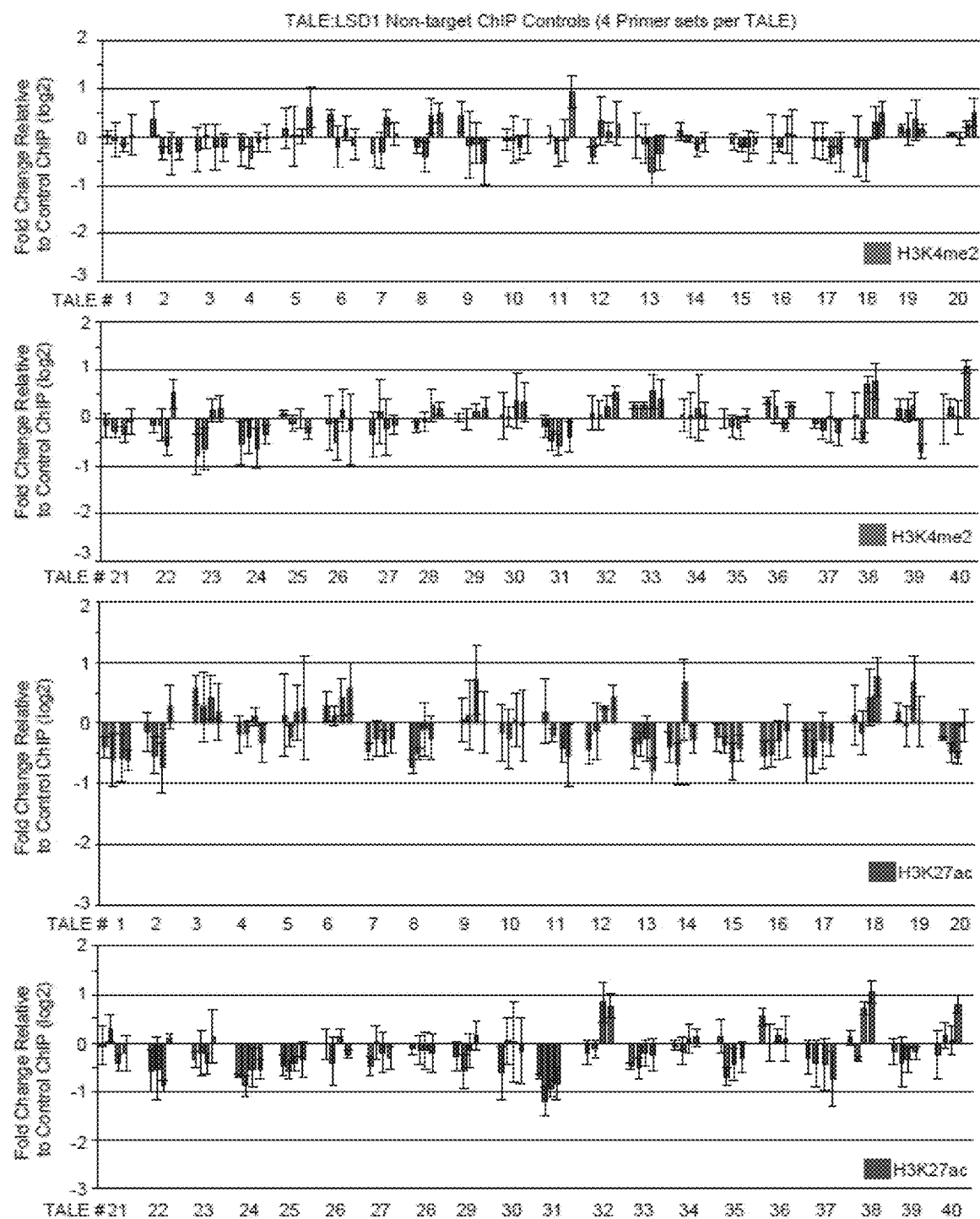
FIG. 5. ChIP-qPCR for H3K4me2 and H3K27ac at non-target sites. Data is shown for all 40 TALE-LSD1 constructs used in FIG. 2. Four primers sets were used to measure ChIP enrichment at two non-target enhancer loci for each TALE construct. No non-target enhancer showed a significant decrease (>2 fold decrease in 2/4 primer sets) in ChIP enrichment.
Figure 6:
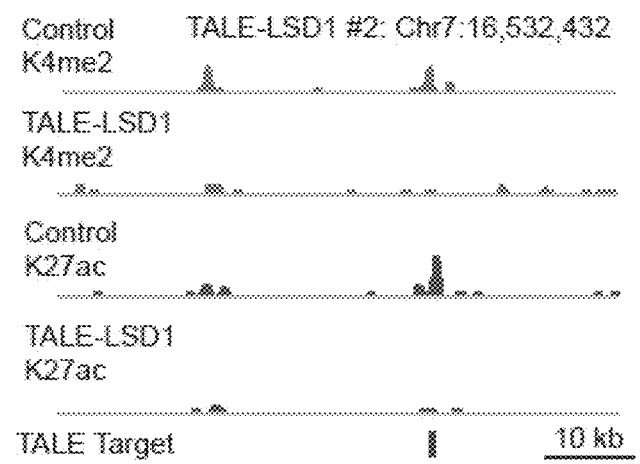
FIG. 6. ChIP-seq maps for H3K4me2 and H3K27ac for control cells and cells transfected independently with 2 TALE-LSD1 fusions.
Figure 6:
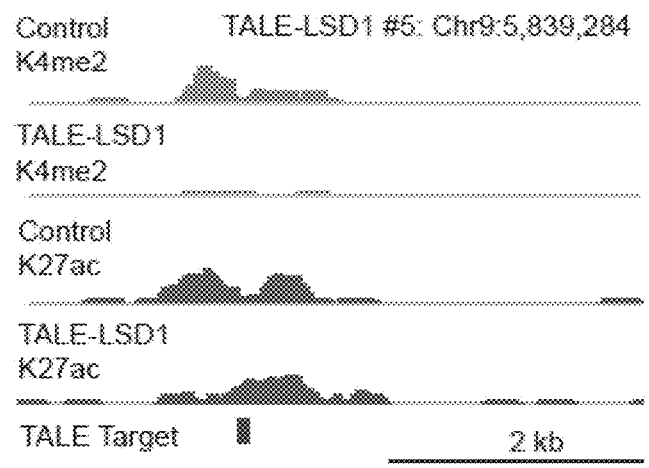

26 of the 40 TALE-LSD1 constructs (65%) significantly reduced levels of these modifications at their target loci, relative to control transfected cells (FIG. 2). An additional 8 constructs caused more modest reductions at their targets, suggesting that the strategy can be effective at most enhancers (FIG. 2). ChIP-qPCR measurements of H3K4me1 and H3K4me3 confirm that the reagents also reduce these alternative H3K4 methylation states (FIGS. 4A-C). The induced changes were specific to the target loci, as analogous measurements at non-target enhancers did not reveal substantial changes (FIG. 5). Furthermore, genome-wide ChIP-seq analysis of two TALE-LSD1 fusions that were positive by ChIPqPCR confirmed the robustness and specificity with which they reduce chromatin signals at target loci (FIG. 6). These results suggest that TALE-LSD1 fusions can provide an effective means for inactivating chromatin at any target enhancer.

TABLE 1

TALE Array Target Sequences

| TALE ID# | chr # | TALE Target Sequence | SEQ ID NO: |
|---|---|---|---|
| 1 | chr12:25,845,475 | TTCAGTTGTGGTATCTG | 6 |
| 2 | chr7:16,532,432 | TACCATGTCTTTCTAAG | 7 |

TABLE 1-continued

TALE Array Target Sequences

| TALE ID# | chr # | TALE Target Sequence | SEQ ID NO: |
|---|---|---|---|
| 3 | chr3:141,765,325 | TTTACAGAGCTGTGGTCACT | 8 |
| 4 | chr1:47,647,018 | TCCGTGGCTGCCAGTCTG | 9 |
| 5 | chr9:5,839,284 | TGCATATACTTTTTAATG | 10 |
| 6 | chr1:47,646,996 | TCCAGGAGCGCGCCTGAG | 11 |
| 7 | chr7:129,598,655 | TGCCTGTGAGGAACAGCTGT | 12 |
| 8 | chr2:169,708,409 | TGCAGACATCTCCAGGCTCT | 13 |
| 9 | chr9:102,832,599 | TAATTTGTACATGGTTACAT | 14 |
| 10 | chr15:38,894,009 | TGTTAGTTACCATATTGTGG | 15 |
| 11 | chr8:106,347,824 | TCCAGTCCCTGGCTCCCATG | 16 |
| 12 | chr16:10,832,743 | TGGCTAATTTTTGGTATTTT | 17 |
| 13 | chr4:145,245,496 | TGGCTTTCCTTCCCTTTG | 18 |
| 14 | chrX:49,023,709 | TAGCCGCGAGGAAGGCG | 19 |
| 15 | chr5:162,806,718 | TAAAGACCTGTTACCCAATT | 20 |
| 16 | chr4:145,050,452 | TCGTTTTCTTTTTTGGAAG | 21 |
| 17 | chr7:129,515,859 | TTCTAAATTGAGGTGCTG | 22 |
| 18 | chr10:11,183,638 | TCAATCATTGCATGTTTATT | 23 |
| 19 | chr17:8,323,819 | TTGCATCTGGGACAGATG | 24 |
| 20 | chr11:5,245,852 | TTGATGGTAACACTATG | 25 |
| 21 | chr1:182,269,308 | TTATCTCCCTCACCCAG | 26 |
| 22 | chr1:198,568,183 | TGGTTAGAAACACAGCTGCC | 27 |
| 23 | chr6:138,240,975 | TTCATGGTTCAATAAAGACT | 28 |
| 24 | chr3:150,169,053 | TACATAAAATTTTTAAGG | 29 |
| 25 | chr8:106,341,287 | TTAAGCTTCTGAAGTCAG | 30 |
| 26 | chrX:119,619,445 | TGATCTTCATTTTTAAAG | 31 |
| 27 | chr21:15,825,632 | TGGTATGAGTTGAAAATG | 32 |
| 28 | chr8:106,376,850 | TAAGTCTACATATAGTATCC | 33 |
| 29 | chr11:16,617,852 | TAAAATGCACTCACAATG | 34 |
| 30 | chr19:14,496,304 | TCTCTGAATCCCCTGGTGAC | 35 |
| 31 | chr6:119,634,206 | TTAAACAGATAAGGGAG | 36 |
| 32 | chr1:47,646,977 | TGGTGCGTTATCAGCCTT | 37 |
| 33 | chr8:106,256,324 | TCAATACCCCACAAAGAAGC | 38 |
| 34 | chr20:36,007,695 | TCTCTACCTTGGAGGCTG | 39 |
| 35 | chr1:166,674,281 | TAGAAAATACAACCTCAG | 40 |
| 36 | chr11:48,082,936 | TCCTGGAAAGCCCTCTATG | 41 |
| 37 | chr14:23,030,549 | TAAGTTTGCAAACAAGCTCC | 42 |
| 38 | chr19:23,907,083 | TGGCTTTCCTAGGCAGAAGT | 43 |
| 39 | chr10:80,948,325 | TCACGCCTTTGTGGCCAGAG | 44 |

TABLE 1-continued

TALE Array Target Sequences

| TALE ID# | chr # | TALE Target Sequence | SEQ ID NO: |
|---|---|---|---|
| 40 | chr18:32,630,094 | TCACTGTGTACCTTTTTATG | 45 |
| non-Target | N/A | TGCAGTGCTTCAGCCGCT | 46 |

Example 5

Next, whether reduced chromatin activity at specific enhancers affects the transcriptional output of nearby genes was considered. These experiments initially focused on 9 TALE-LSD1 fusions that robustly alter chromatin state (FIG. 2), and systematically screened for regulated genes using a modified RNA-seq procedure termed 3' Digital Gene Expression (3'DGE). By only sequencing the 3' ends of mRNAs, this procedure enables quantitative analysis of transcript levels at modest sequencing depths25 as described above. A gene was scored as regulated if (i) it was detected in control K562 cells with a normalized RNA-seq value>10, i.e. the top $50^{th}$ percentile of expression; (ii) its mean expression value was at least 1.5-fold lower in the corresponding on-target TALE-LSD1 libraries compared to all other libraries, p<0.05 calculated using DESeq[26] and (iii) its normalized 3'DGE values in the on-target TALE-LSD1 libraries were the two lowest over all 22 datasets.

The 9 TALEs were transfected individually into K562 cells, alongside with control mCherry plasmids and measured mRNA levels in biological replicate. Each 3'DGE dataset was normalized based on a negative binomial distribution and excluded any libraries that did not satisfy quality controls as described above and in[26]. Whether any of the TALE-LSD1 reagents significantly altered the expression of genes in the vicinity of its target enhancer was then examined.

Figure 3A:
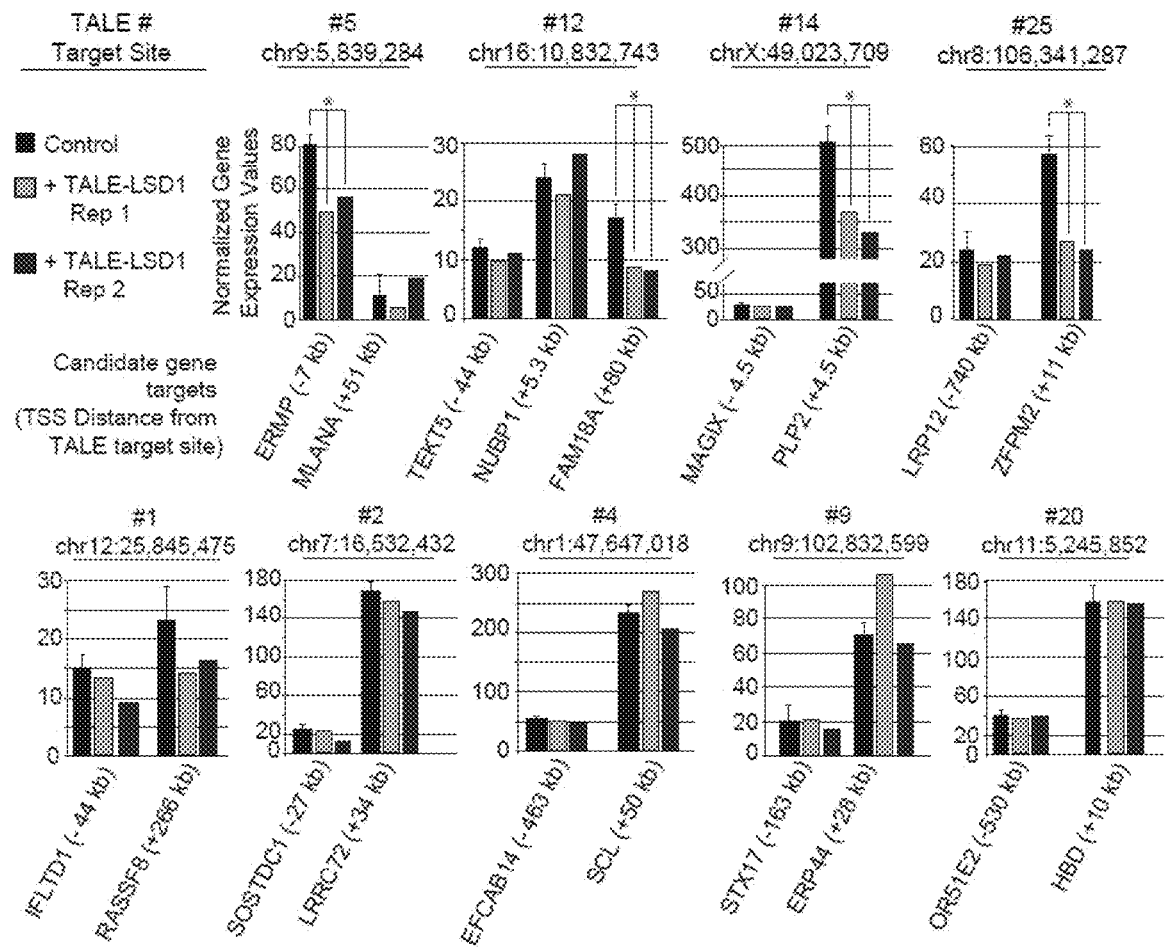
FIGS. 3A-3C. TALE-LSD1 fusions to endogenous enhancers affect proximal gene expression.
Figure 7:
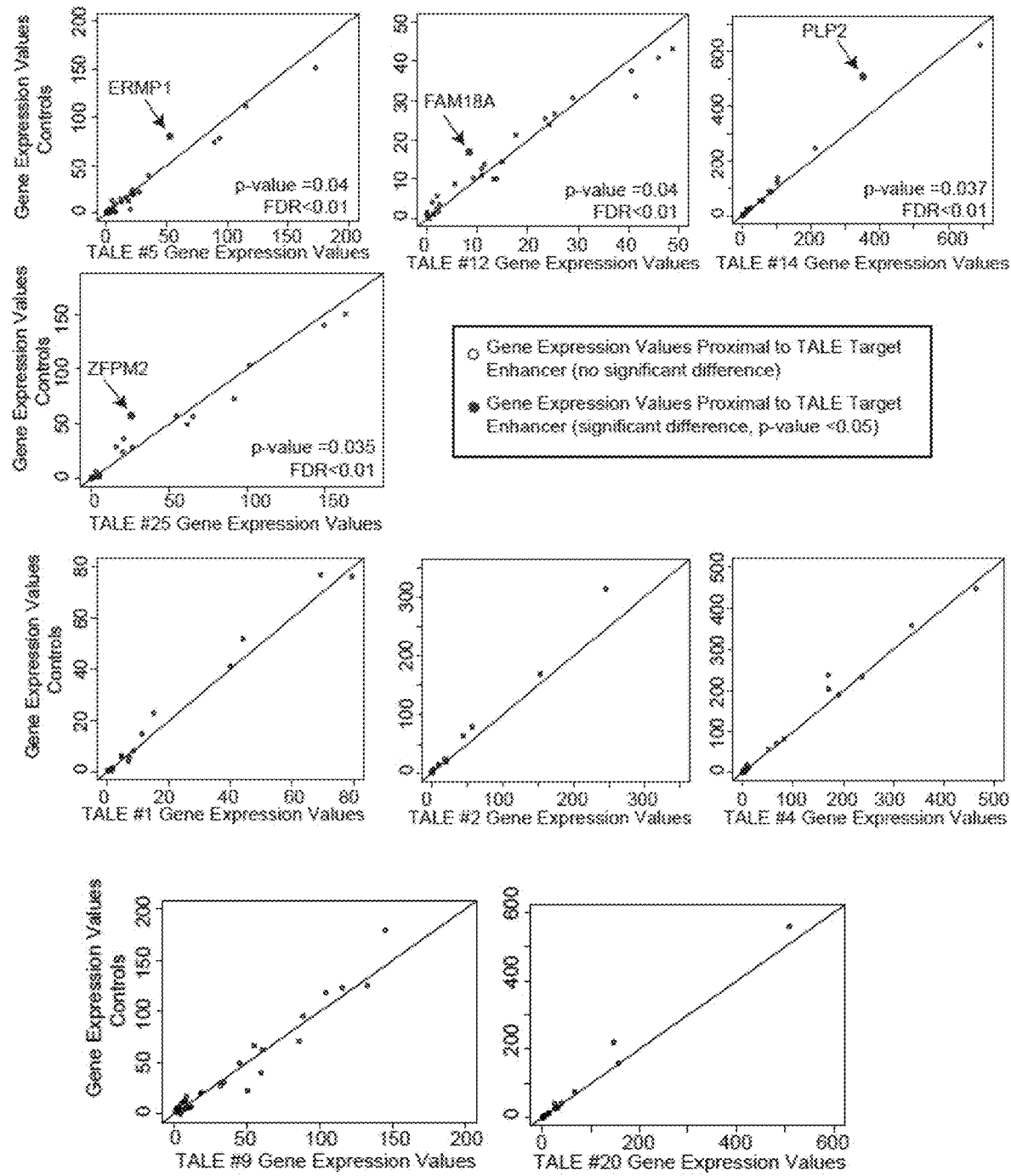
FIG. 7. Mean normalized 3' Digital Gene Expression Values for the 10-25 genes nearest the TALE target enhancer. Genes with values below 10 were considered unexpressed in K562 cells. Data points indicated with arrows and filled circles represent genes with a significant decrease in the TALE-LSD1 transfected cells. Significant decrease was considered if both biological replicates represented the two outlying values across all 22 RNA-seq datasets (see Methods).
Figure 8A:
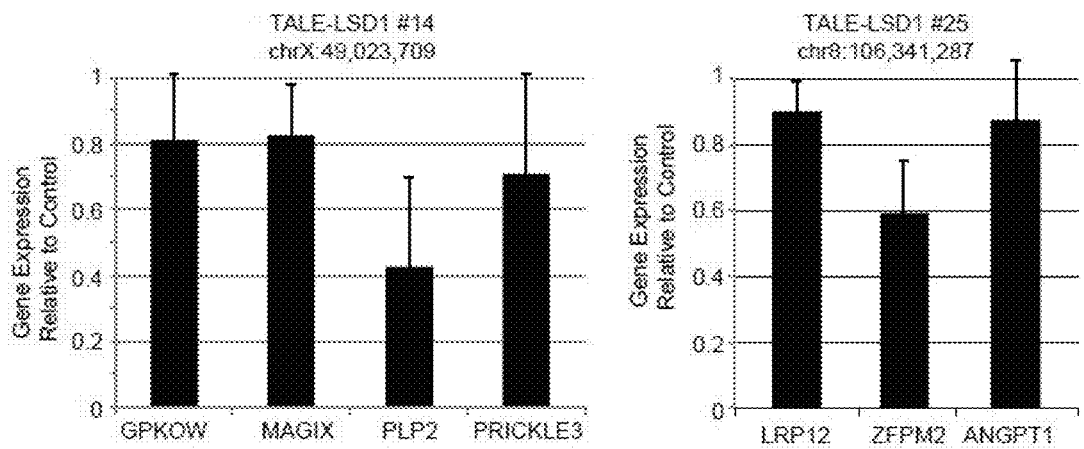
FIGS. 8A-8B. Quantitative PCR confirmation of 3' DGE.
Figure 8B:
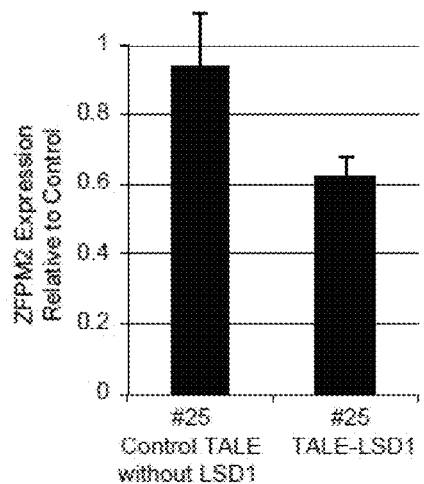

Four of the nine tested fusions (44%) caused a nearby gene to be down-regulated by at least 1.5-fold, with both biological replicates representing the two outlying values across all 22 RNA-seq datasets (see Methods, FIG. 3A, FIG. 7). The significance of these transcriptional changes is supported by a simulated analysis of a random sampling of 1000 genomic locations that did not yield any false-positives in which an adjacent gene scored as regulated (FDR<0.1%). The expression changes were also confirmed by quantitative RT-PCR (FIG. 8A). Two of the enhancers that significantly regulated genes are intergenic, while a third coincides with the 3' end of a gene, but affects the activity of the next downstream gene. The fourth scoring enhancer resides in the first intron of ZFPM2. A TALE lacking the demethylase did not affect ZFPM2 expression, confirming that ZFPM2 down-regulation requires LSD1 recruitment (FIG. 8B). It was not possible to distinguish whether the other five putative enhancers have weak transcriptional effects below the detection threshold or, alternatively, do not regulate any genes in K562 cells. Regardless, these results indicate that TALE-LSD1 fusions can alter enhancer activity in a targeted, loss-of-function manner, and thereby enable identification and modulation of their target genes.

Example 6

Figure 3B:
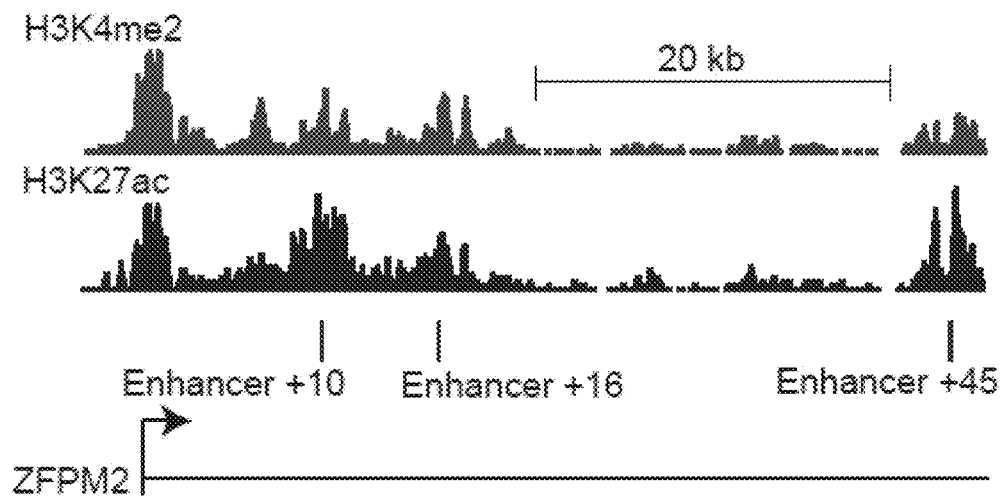
Figure 3C:
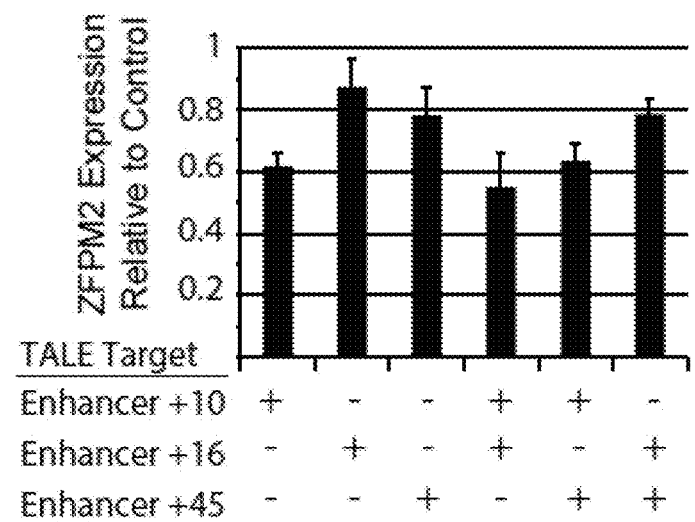

The high prevalence of putative enhancers in the genome suggests that many act redundantly or function only in specific contexts, which could explain our inability to assign target genes to roughly half of the tested elements. To address the former, three putative enhancers were examined within the developmental locus encoding ZFPM2 (FIG. 3B). In addition to the TALE-LSD1 fusion targeted to the intronic enhancer described above (FIGS. 3A, 3B; enhancer +10), TALE-LSD1 fusions were designed and validated that reduced modification levels at two additional intronic ZFPM2 enhancers (enhancers +16, +45) (FIGS. 2, 3B). First, each TALE-LSD1 fusion was transfected individually and their effects on ZFPM2 expression tested by qPCR. While the fusion targeting the original +10 enhancer reduced ZFPM2 expression by ~2-fold, the fusions targeting the +16 and +45 enhancers showed only modest reductions of ~13% and ~22%, respectively, which did not reach statistical significance (FIG. 3C). To determine if these enhancers act additively or synergistically, the fusions were transfected in pairwise combinations. Although targeting pairs of enhancers tended to reduce gene expression more than hitting a single enhancer, the cumulative effects were substantially less than the sum of the two individual effects. This suggests that the multiple enhancers in this locus function redundantly to maintain ZFPM2 expression in K562 cells. These results indicate the potential of programmable TALE-LSD1 fusions to shed light on complex regulatory interactions among multiple enhancers and genes in a locus.

REFERENCES

1. Bulger, M. & Groudine, M. Functional and mechanistic diversity of distal transcription enhancers. Cell 144, 327-339 (2011).
2. Visel, A., Rubin, E. M. & Pennacchio, L. A. Genomic views of distant-acting enhancers. Nature 461, 199-205 (2009).
3. Noonan, J. P. & McCallion, A. S. Genomics of long-range regulatory elements. Annu Rev Genomics Hum Genet 11, 1-23 (2010).
4. Heintzman, N. D. et al. Histone modifications at human enhancers reflect global cell-type-specific gene expression. Nature 459, 108-112 (2009).
5. Boyle, A. P. et al. High-resolution mapping and characterization of open chromatin across the genome. Cell 132, 311-322 (2008).
6. Ernst, J. et al. Mapping and analysis of chromatin state dynamics in nine human cell types. Nature 473, 43-49 (2011).
7. Consortium, T. E. P. et al. An integrated encyclopedia of DNA elements in the human genome. Nature 488, 57-74 (2012).
8. Maurano, M. T. et al. Systematic localization of common disease-associated variation in regulatory DNA. Science 337, 1190-1195 (2012).
9. Calo, E. & Wysocka, J. Modification of Enhancer Chromatin: What, How, and Why? MOLCEL 49, 825-837 (2013).

10. Stadler, M. B. et al. DNA-binding factors shape the mouse methylome at distal regulatory regions. Nature 480, 490-495 (2011).
11. Ng, J.-H. et al. In vivo epigenomic profiling of germ cells reveals germ cell molecular signatures. Dev Cell 24, 324-333 (2013).
12. Creyghton, M. P. et al. Histone H3K27ac separates active from poised enhancers and predicts developmental state. Proceedings of the National Academy of Sciences 107, 21931-21936 (2010).
13. Rada-Iglesias, A. et al. A unique chromatin signature uncovers early developmental enhancers in humans. Nature 470, 279-283 (2011).
14. Shi, Y. et al. Histone Demethylation Mediated by the Nuclear Amine Oxidase Homolog LSD1. Cell 119, 941-953 (2004).
15. Boch, J. et al. Breaking the Code of DNA Binding Specificity of TAL-Type III Effectors. Science 326, 1509-1512 (2009).
16. Moscou, M. J. & Bogdanove, A. J. A simple cipher governs DNA recognition by TAL effectors. Science 326, 1501 (2009).
17. Mussolino, C. & Cathomen, T. TALE nucleases: tailored genome engineering made easy. Curr Opin Biotechnol 23, 644-650 (2012).
18. Joung, J. K. & Sander, J. D. TALENs: a widely applicable technology for targeted genome editing. Nat. Rev. Mol. Cell Biol. 14, 49-55 (2013).
19. Dhami, P. et al. Genomic Approaches Uncover Increasing Complexities in the Regulatory Landscape at the Human SCL (TAL1) Locus. PLoS ONE 5, e9059 (2010).
20. Zhang, F. et al. Efficient construction of sequence-specific TAL effectors for modulating mammalian transcription. Nat Biotechnol 29, 149-153 (2011).
21. Lee, M. G., Wynder, C., Cooch, N. & Shiekhattar, R. An essential role for CoREST in nucleosomal histone 3 lysine 4 demethylation. Nature (2005). doi:10.1038/nature04021
22. Whyte, W. A. et al. Enhancer decommissioning by LSD1 during embryonic stem cell differentiation. Nature 1-5 (2012). doi:10.1038/nature10805
23. Reyon, D. et al. FLASH assembly of TALENs for high-throughput genome editing. Nat Biotechnol 30, 460-465 (2012).
24. Yoon, O. K. & Brem, R. B. Noncanonical transcript forms in yeast and their regulation during environmental stress. RNA 16, 1256-1267 (2010).
25. Anders, S. & Huber, W. Differential expression analysis for sequence count data. Genome Biol. 11, R106 (2010).
26. Maeder, M. L. et al. Robust, synergistic regulation of human gene expression using TALE activators. Nat Meth 10, 243-245 (2013).
27. Ku, M. et al. Genomewide analysis of PRC1 and PRC2 occupancy identifies two classes of bivalent domains. PLoS Genet. 4, e1000242 (2008).
28. Ram, 0. et al. Combinatorial Patterning of Chromatin Regulators Uncovered by Genome-wide Location Analysis in Human Cells. Cell 147, 1628-1639 (2011).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion protein comprising
an engineered transcription activator-like (TAL) effector repeat array that binds specifically to the nucleic acid sequence set forth in SEQ ID NO:10, and
a catalytic domain comprising a sequence that catalyzes histone demethylation.

2. The fusion protein of claim 1, further comprising a linker between the engineered TAL effector repeat array and the catalytic domain.

3. The fusion protein of claim 1, wherein the catalytic domain comprises full length lysine-specific demethylase 1 (LSD1), or a catalytic domain of LSD1.

4. The fusion protein of claim 3, wherein the catalytic domain comprises amino acids 172-833 of SEQ ID NO:1.

5. The fusion protein of claim 1, comprising a plurality of catalytic domains, optionally with linkers therebetween.

* * * * *

SEQUENCE LISTING

```
<160> NUMBER OF SEQ ID NOS: 226

<210> SEQ ID NO 1
<211> LENGTH: 852
<212> TYPE: PRT
<213> ORGANISM: Homo sapiens

<400> SEQUENCE: 1

Met Leu Ser Gly Lys Lys Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140
```

```
Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Val Glu Gly
                165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
            195                 200                 205

Val Phe Leu Phe Ile Arg Asn Arg Thr Leu Gln Leu Trp Leu Asp Asn
210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Gly Ser Gly Val
            275                 280                 285

Ser Gly Leu Ala Ala Ala Arg Gln Leu Gln Ser Phe Gly Met Asp Val
290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
                325                 330                 335

Leu Gly Gly Asn Pro Met Ala Val Val Ser Lys Gln Val Asn Met Glu
            340                 345                 350

Leu Ala Lys Ile Lys Gln Lys Cys Pro Leu Tyr Glu Ala Asn Gly Gln
            355                 360                 365

Ala Val Pro Lys Glu Lys Asp Glu Met Val Glu Gln Glu Phe Asn Arg
370                 375                 380

Leu Leu Glu Ala Thr Ser Tyr Leu Ser His Gln Leu Asp Phe Asn Val
385                 390                 395                 400

Leu Asn Asn Lys Pro Val Ser Leu Gly Gln Ala Leu Glu Val Val Ile
                405                 410                 415

Gln Leu Gln Glu Lys His Val Lys Asp Glu Gln Ile Glu His Trp Lys
            420                 425                 430

Lys Ile Val Lys Thr Gln Glu Glu Leu Lys Glu Leu Leu Asn Lys Met
            435                 440                 445

Val Asn Leu Lys Glu Lys Ile Lys Glu Leu His Gln Gln Tyr Lys Glu
            450                 455                 460

Ala Ser Glu Val Lys Pro Pro Arg Asp Ile Thr Ala Glu Phe Leu Val
465                 470                 475                 480

Lys Ser Lys His Arg Asp Leu Thr Ala Leu Cys Lys Glu Tyr Asp Glu
                485                 490                 495

Leu Ala Glu Thr Gln Gly Lys Leu Glu Glu Lys Leu Gln Glu Leu Glu
            500                 505                 510

Ala Asn Pro Pro Ser Asp Val Tyr Leu Ser Ser Arg Asp Arg Gln Ile
            515                 520                 525

Leu Asp Trp His Phe Ala Asn Leu Glu Phe Ala Asn Ala Thr Pro Leu
530                 535                 540

Ser Thr Leu Ser Leu Lys His Trp Asp Gln Asp Asp Asp Phe Glu Phe
545                 550                 555                 560
```

```
Thr Gly Ser His Leu Thr Val Arg Asn Gly Tyr Ser Cys Val Pro Val
            565                 570                 575

Ala Leu Ala Glu Gly Leu Asp Ile Lys Leu Asn Thr Ala Val Arg Gln
        580                 585                 590

Val Arg Tyr Thr Ala Ser Gly Cys Glu Val Ile Ala Val Asn Thr Arg
    595                 600                 605

Ser Thr Ser Gln Thr Phe Ile Tyr Lys Cys Asp Ala Val Leu Cys Thr
610                 615                 620

Leu Pro Leu Gly Val Leu Lys Gln Gln Pro Ala Val Gln Phe Val
625                 630                 635                 640

Pro Pro Leu Pro Glu Trp Lys Thr Ser Ala Val Gln Arg Met Gly Phe
                645                 650                 655

Gly Asn Leu Asn Lys Val Val Leu Cys Phe Asp Arg Val Phe Trp Asp
            660                 665                 670

Pro Ser Val Asn Leu Phe Gly His Val Gly Ser Thr Thr Ala Ser Arg
        675                 680                 685

Gly Glu Leu Phe Leu Phe Trp Asn Leu Tyr Lys Ala Pro Ile Leu Leu
    690                 695                 700

Ala Leu Val Ala Gly Glu Ala Ala Gly Ile Met Glu Asn Ile Ser Asp
705                 710                 715                 720

Asp Val Ile Val Gly Arg Cys Leu Ala Ile Leu Lys Gly Ile Phe Gly
                725                 730                 735

Ser Ser Ala Val Pro Gln Pro Lys Glu Thr Val Val Ser Arg Trp Arg
            740                 745                 750

Ala Asp Pro Trp Ala Arg Gly Ser Tyr Ser Tyr Val Ala Ala Gly Ser
        755                 760                 765

Ser Gly Asn Asp Tyr Asp Leu Met Ala Gln Pro Ile Thr Pro Gly Pro
    770                 775                 780

Ser Ile Pro Gly Ala Pro Gln Pro Ile Pro Arg Leu Phe Phe Ala Gly
785                 790                 795                 800

Glu His Thr Ile Arg Asn Tyr Pro Ala Thr Val His Gly Ala Leu Leu
                805                 810                 815

Ser Gly Leu Arg Glu Ala Gly Arg Ile Ala Asp Gln Phe Leu Gly Ala
            820                 825                 830

Met Tyr Thr Leu Pro Arg Gln Ala Thr Pro Gly Val Pro Ala Gln Gln
        835                 840                 845

Ser Pro Ser Met
    850

<210> SEQ ID NO 2
<211> LENGTH: 876
<212> TYPE: PRT
<213> ORGANISM: Homo sapiens

<400> SEQUENCE: 2

Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80
```

```
Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
                100                 105                 110

Arg Lys Arg Ala Lys Val Glu Tyr Arg Glu Met Asp Glu Ser Leu Ala
                115                 120                 125

Asn Leu Ser Glu Asp Glu Tyr Tyr Ser Glu Glu Arg Asn Ala Lys
            130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Gln Ala Gly
                165                 170                 175

Gly Leu Gln Asp Asp Ser Ser Gly Gly Tyr Gly Asp Gly Gln Ala Ser
                180                 185                 190

Gly Val Glu Gly Ala Ala Phe Gln Ser Arg Leu Pro His Asp Arg Met
            195                 200                 205

Thr Ser Gln Glu Ala Ala Cys Phe Pro Asp Ile Ile Ser Gly Pro Gln
        210                 215                 220

Gln Thr Gln Lys Val Phe Leu Phe Ile Arg Asn Arg Thr Leu Gln Leu
225                 230                 235                 240

Trp Leu Asp Asn Pro Lys Ile Gln Leu Thr Phe Glu Ala Thr Leu Gln
                245                 250                 255

Gln Leu Glu Ala Pro Tyr Asn Ser Asp Thr Val Leu Val His Arg Val
            260                 265                 270

His Ser Tyr Leu Glu Arg His Gly Leu Ile Asn Phe Gly Ile Tyr Lys
        275                 280                 285

Arg Ile Lys Pro Leu Pro Thr Lys Lys Thr Gly Lys Val Ile Ile Ile
290                 295                 300

Gly Ser Gly Val Ser Gly Leu Ala Ala Ala Arg Gln Leu Gln Ser Phe
305                 310                 315                 320

Gly Met Asp Val Thr Leu Leu Glu Ala Arg Asp Arg Val Gly Gly Arg
                325                 330                 335

Val Ala Thr Phe Arg Lys Gly Asn Tyr Val Ala Asp Leu Gly Ala Met
            340                 345                 350

Val Val Thr Gly Leu Gly Gly Asn Pro Met Ala Val Val Ser Lys Gln
        355                 360                 365

Val Asn Met Glu Leu Ala Lys Ile Lys Gln Lys Cys Pro Leu Tyr Glu
        370                 375                 380

Ala Asn Gly Gln Ala Asp Thr Val Lys Val Pro Lys Glu Lys Asp Glu
385                 390                 395                 400

Met Val Glu Gln Glu Phe Asn Arg Leu Leu Glu Ala Thr Ser Tyr Leu
                405                 410                 415

Ser His Gln Leu Asp Phe Asn Val Leu Asn Asn Lys Pro Val Ser Leu
            420                 425                 430

Gly Gln Ala Leu Glu Val Val Ile Gln Leu Gln Glu Lys His Val Lys
        435                 440                 445

Asp Glu Gln Ile Glu His Trp Lys Lys Ile Val Lys Thr Gln Glu Glu
        450                 455                 460

Leu Lys Glu Leu Leu Asn Lys Met Val Asn Leu Lys Glu Lys Ile Lys
465                 470                 475                 480

Glu Leu His Gln Gln Tyr Lys Glu Ala Ser Glu Val Lys Pro Pro Arg
                485                 490                 495
```

-continued

Asp Ile Thr Ala Glu Phe Leu Val Lys Ser Lys His Arg Asp Leu Thr
                500                 505                 510

Ala Leu Cys Lys Glu Tyr Asp Glu Leu Ala Glu Thr Gln Gly Lys Leu
            515                 520                 525

Glu Glu Lys Leu Gln Glu Leu Glu Ala Asn Pro Pro Ser Asp Val Tyr
        530                 535                 540

Leu Ser Ser Arg Asp Arg Gln Ile Leu Asp Trp His Phe Ala Asn Leu
545                 550                 555                 560

Glu Phe Ala Asn Ala Thr Pro Leu Ser Thr Leu Ser Leu Lys His Trp
                565                 570                 575

Asp Gln Asp Asp Phe Glu Phe Thr Gly Ser His Leu Thr Val Arg
            580                 585                 590

Asn Gly Tyr Ser Cys Val Pro Val Ala Leu Ala Glu Gly Leu Asp Ile
        595                 600                 605

Lys Leu Asn Thr Ala Val Arg Gln Val Arg Tyr Thr Ala Ser Gly Cys
610                 615                 620

Glu Val Ile Ala Val Asn Thr Arg Ser Thr Ser Gln Thr Phe Ile Tyr
625                 630                 635                 640

Lys Cys Asp Ala Val Leu Cys Thr Leu Pro Leu Gly Val Leu Lys Gln
                645                 650                 655

Gln Pro Pro Ala Val Gln Phe Val Pro Pro Leu Pro Glu Trp Lys Thr
            660                 665                 670

Ser Ala Val Gln Arg Met Gly Phe Gly Asn Leu Asn Lys Val Val Leu
        675                 680                 685

Cys Phe Asp Arg Val Phe Trp Asp Pro Ser Val Asn Leu Phe Gly His
690                 695                 700

Val Gly Ser Thr Thr Ala Ser Arg Gly Glu Leu Phe Leu Phe Trp Asn
705                 710                 715                 720

Leu Tyr Lys Ala Pro Ile Leu Leu Ala Leu Val Ala Gly Glu Ala Ala
                725                 730                 735

Gly Ile Met Glu Asn Ile Ser Asp Asp Val Ile Val Gly Arg Cys Leu
            740                 745                 750

Ala Ile Leu Lys Gly Ile Phe Gly Ser Ser Ala Val Pro Gln Pro Lys
        755                 760                 765

Glu Thr Val Val Ser Arg Trp Arg Ala Asp Pro Trp Ala Arg Gly Ser
770                 775                 780

Tyr Ser Tyr Val Ala Ala Gly Ser Ser Gly Asn Asp Tyr Asp Leu Met
785                 790                 795                 800

Ala Gln Pro Ile Thr Pro Gly Pro Ser Ile Pro Gly Ala Pro Gln Pro
                805                 810                 815

Ile Pro Arg Leu Phe Phe Ala Gly Glu His Thr Ile Arg Asn Tyr Pro
            820                 825                 830

Ala Thr Val His Gly Ala Leu Leu Ser Gly Leu Arg Glu Ala Gly Arg
        835                 840                 845

Ile Ala Asp Gln Phe Leu Gly Ala Met Tyr Thr Leu Pro Arg Gln Ala
850                 855                 860

Thr Pro Gly Val Pro Ala Gln Gln Ser Pro Ser Met
865                 870                 875

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gttcaagatc tttatctggg aagaaggcgg                                30

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaccttaatt aaatgggcct cttcccttag aa                             32

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Ser Gly Gly Ser Gly Gly Ser
1               5

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttcagttgtg gtatctg                                              17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taccatgtct ttctaag                                              17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttacagagc tgtggtcact                                           20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tccgtggctg ccagtctg                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgcatatact ttttaatg                                                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tccaggagcg cgcctgag                                                18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcctgtgag gaacagctgt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgcagacatc tccaggctct                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taatttgtac atggttacat                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgttagttac catattgtgg                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tccagtccct ggctcccatg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggctaattt ttggtatttt                                                    20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tggctttcct tccctttg                                                      18

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tagccgcgag gaaggcg                                                       17

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
taaagacctg ttacccaatt                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 tcgttttttct tttttggaag                                              20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttctaaattg aggtgctg                                                 18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcaatcattg catgtttatt                                               20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttgcatctgg gacagatg                                                 18

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttgatggtaa cactatg                                                  17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttatctccct cacccag                                                  17

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tggttagaaa cacagctgcc                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttcatggttc aataaagact                                          20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tacataaaat ttttaagg                                            18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttaagcttct gaagtcag                                            18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgatcttcat ttttaaag                                            18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tggtatgagt tgaaaatg                                            18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
taagtctaca tatagtatcc                                           20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
taaaatgcac tcacaatg                                             18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tctctgaatc ccctggtgac                                           20

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttaaacagat aagggag                                              17

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tggtgcgtta tcagcctt                                             18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcataccccc acaaagaagc                                           20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tctctacctt ggaggctg                                             18

```
<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tagaaaatac aacctcag                                                   18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcctggaaaa gccctctatg                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
taagtttgca aacaagctcc                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tggctttcct aggcagaagt                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcacgccttt gtggccagag                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcactgtgta ccttttttatg                                                20
```

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgcagtgctt cagccgct                                                 18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaatcgtga atacccctga                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aacatgcagg tctgctttcc                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggaattggcc tgcagaatta                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtacaccatt ggctggctct                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tactgaccca tgagcacagc                                               20

```
<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccccactgcc atcctactta                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gagtgttggc agaatgagca                                              20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgtgcgtatg cattttgttc t                                            21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agcacacaat tttgctcatc a                                            21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgtgcacat ggaacaagac                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctgccaagtt tctggttggt                                              20

<210> SEQ ID NO 58
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagacaaaat agcggggaca                                                 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aagaggacat tctgggctga                                                 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cctgcctcct aagcttcctt                                                 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gacctgactc gaacccactc                                                 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcctctgcta aggcacaaac                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgcctaggaa ggcacttgtc                                                 20

<210> SEQ ID NO 64
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggctggagat cagcttttg                                                     20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgtcctggaa cggtttcact                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tttctccttt gggcatcttg                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aagaggacat tctgggctga                                                    20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cctgcctcct aagcttcctt                                                    20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gacctgactc gaacccactc                                                    20

<210> SEQ ID NO 70
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 70
gcctctgcta aggcacaaac                                                  20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cccttgacca ggtaggttca                                                  20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaggagggct ccagtttcat                                                  20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tggtggaatg agtagcagag c                                                21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggggattttc acacttggtg                                                  20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgtctgcaca aattgctgtg                                                  20

<210> SEQ ID NO 76
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 76
cttgggaggg gttcagagac                                                  20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
actcaaaggt gggtgtgagg                                                  20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tccgataatc tggtccaagg                                                  20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cccaggaaac ttgatgagag a                                                21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tgtggaagga gtgagtgaac a                                                21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gggttttcat gaagctttga a                                                21

<210> SEQ ID NO 82
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 82
tttcgtattg catcccatca                                                20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gctgagcttt tcaggtaggc                                                20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gctcccaaaa agatgcaagt                                                20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gggccctcct tatacttgga                                                20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tggactggga ggaacatagc                                                20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgctacgtgc agcgtattct                                                20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 88
tgcaacgcta tttctcagga                                        20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
agcattttca gcctcagtgg                                        20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccttgtagca cctctgtcca                                        20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cagacttctg gaacgcagtg                                        20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgtgacaggc caagtctcag                                        20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ctgacggttt atgagcagca                                        20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtttcccaca gttccctgaa        20

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tgaagtccac atgtttagct cct        23

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tggaaggaat gtgattccac t        21

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ttcaacagca accaggaatg        20

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aagctcaaaa agaaaaactt caaca        25

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ccattttccg tacatggtga        20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctggctgtag ggctctgttc					20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gacggggaag gaagaaagaa					20

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tcccagctct cgcagctt					18

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tacacaacag cacccacaca					20

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ccccatttca gttctttctc a					21

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tcttctgggt ttgttggcta					20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggcaccatgt gaactctcct                                             20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tccaactcaa tgccttttct g                                           21

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cacaggcaag attcccattt                                             20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aatggctctg gagaaaagca                                             20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcatgccagt ctgaagatga                                             20

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tgtgaacctc gagaagtgtg a                                           21

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ttgttgaggt gtgcatgagg                                           20

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gtcatgtcca gcaggatgc                                            19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
atgcagctga cccattgttt                                           20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acgatggagg acattggaag                                           20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tgaaggcttt tcaggagctt                                           20

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ctgcaaacaa ggtctttgga c                                         21

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aggcagctac ctggttaagg                                           20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gtgaccttgg agacgttgct                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agcctcttga accagagcag                                              20

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aagagaagga gaaccaagcc tta                                          23

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cacaccagca aagagcaaaa                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gattccgggt cactgtgagt                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ttttacggcg agatggtttc                                              20

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ggaagaaagg aaggtaggaa gg                                            22

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
agggcactct cctctcctct                                               20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gctgagacca cccactcttc                                               20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cccagaagga attacccaca                                               20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tcacacatca cttgcgttca                                               20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tggcttgata acccaaccat                                               20

```
<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
agggagcact ctagggatgg                                                   20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132 cagggaaac aggaagtgag                                                    20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccactaaacc gcaaccaaag                                                   20

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ggaaactccc agctttcaaa c                                                 21

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgtttctccc tgggttcttt                                                   20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
atttttctgc ctcccaaacc                                                   20

<210> SEQ ID NO 137
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
ctgcccccaa agaaaggtat          20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
ttggcatact tcatgctcac a          21

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
ttgacattag gtccaggttt ga          22

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
tattttaggg caggcacacc          20

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
tcattttggt agcctttctg c          21

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
cactcaagtc ccaggttggt          20

<210> SEQ ID NO 143
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gatgatttgg cttttgcgat a                                            21

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cttgtgggag ctcgacatta                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gacgtgttgg tgcatacctg                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
atgaggctcc tccctcattt                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
tcaagagtac ggcaatcacg                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gggaaaccga aggattgatt                                              20

<210> SEQ ID NO 149
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 149
gaccaccggt cttctcatgt                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gcagctgatg aagagcagaa                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tagggtgtgg atgtggaaca                                              20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tgggaaattg ctgtgttgag                                              20

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tcctgtaaag tcctcagatc aaca                                         24

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gccagcttct aaggatgcac                                              20

<210> SEQ ID NO 155
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 155
ttggtctttg gccttctagg                                              20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
aatggggaag tgacaaggaa                                              20

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cagcctttct aggaatcaca aa                                           22

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ggatgatgag gaactggctt t                                            21

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtgaaccacc aagcacagc                                               19

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
agcaggggtg gagagaaaat                                              20

<210> SEQ ID NO 161
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 161
ggctacagcg tcttcctgtg                                                 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cacacaccac acccacaact                                                 20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
taaggccggt ctatcacagc                                                 20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcagtctcag cacctcaacc                                                 20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
actgcctgcc tggagtctac                                                 20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tcgctcactg aggaatgatg                                                 20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
tacaccgcga agggatagtc                                           20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tgggggtcag agagagaatg                                           20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggccccaga ctttaatttg                                           20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcctctggag tgcagtacct                                           20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cccagatatt tcctgctcca                                           20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cccccaaatt ccattattcc                                           20

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gagggagcga gccatagtg					19

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
acaatggggc tgcctgag					18

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggaggagggt ggtctctcat					20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tcgaaagcta cacggctctt					20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tgggtgagga aggagaaaga					20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
aaacccctat gggcaactct					20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ctggccctct tctcctttct                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
caatcatttg ccaacacagg                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gtctgaggaa aggcacctga                                               20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tcgcacctgt gtgagaggta                                               20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
agcgacaaaa ggtcaacaga                                               20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ggtgttgcgg aaaacacttt                                               20

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cctaagaatc agaaacgcaa tg                                           22

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cagtctgggc aacagaacaa                                              20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
aacgaaacac aacctgcaca                                              20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ctgtaaccct acccccaacc                                              20

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cagaacaaaa tggagtctta gcc                                          23

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tcagaaggtg tggggaaaag                                              20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191

```
atggctttca tgaagctgga                                                   20

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cgtctgtgcg aagagaagc                                                    19

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
aaagcatttt tgccatccag                                                   20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ttcccggtta gatgagttgg                                                   20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gccctccctt gataagaacc                                                   20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tgggaacctc tccatctcac                                                   20

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ccaaagtcac atggatgaca g                                                 21
```

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 198
ggctaaatga ggcagatgct                                              20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 199
ctgagggaag acatgctgga                                              20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 200
agtgaagctc caccacctga                                              20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 201
cccagctcca cctggttatt                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 202
ctagggaagt gctgctgctg                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 203
atgtgtgacc tgcacaccaa                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204 ctttaccct gcgacgattt                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ggcaccagca cagagttagc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gacgaccgaa ggcactatca                                              20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gaagctcctc cctcgtatgg                                              20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tccaagctga gatcgtaccg                                              20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
atcagatttc cagcctgtgc                                              20

```
<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tgatcacgga atcagcagtg                                                    20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ctgggacagc aggaaaacag                                                    20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tagattggag gggccacaag                                                    20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ggcctgaaaa tctgagctgc                                                    20

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
cagtcgtctg tctcaactcc a                                                  21

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gtacagcaaa gggggtcagc                                                    20

<210> SEQ ID NO 216
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
gactggcagc ttgtagcctt                                              20

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gttttatctt ttgaaaggca cagtc                                        25

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ttgtgatcac caggtgcagt                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tcaattcagc tgcttcctca                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ctggaaatct gatgggcact                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tctgcactct ggggaagaag                                              20

<210> SEQ ID NO 222
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
caagaatgaa gcaagggaca                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ttccccatga accacagttt                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tgcaatactg gagaggtgga                                              20

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ttaccatgtc tttctaag                                                18

<210> SEQ ID NO 226
<211> LENGTH: 9
<212> TYPE: PRT
<213> ORGANISM: Unknown
<220> FEATURE:
<223> OTHER INFORMATION: Description of Unknown: "LAGLIDADG"
      motif sequence

<400> SEQUENCE: 226

Leu Ala Gly Leu Ile Asp Ala Asp Gly
1               5
```